US009433629B2

(12) United States Patent
Paz Garcia et al.

(10) Patent No.: US 9,433,629 B2
(45) Date of Patent: Sep. 6, 2016

(54) FORMULATION FOR REGENERATION OF BONE, CARTILAGE, TEETH, AND PERIODONTIUM AND TREATMENT OF TUMORS AND CYSTS

(71) Applicants: Juan Paz Garcia, Colima (MX); Brenda Astrid Paz Michel, Bloomington, MN (US)

(72) Inventors: Juan Paz Garcia, Colima (MX); Brenda Astrid Paz Michel, Bloomington, MN (US)

( * ) Notice: Subject to any disclaimer, the term of this patent is extended or adjusted under 35 U.S.C. 154(b) by 0 days.

(21) Appl. No.: 14/809,417

(22) Filed: Jul. 27, 2015

(65) Prior Publication Data

US 2015/0335660 A1    Nov. 26, 2015

Related U.S. Application Data

(63) Continuation-in-part of application No. PCT/US2015/032114, filed on May 22, 2015, which is a continuation-in-part of application No. 14/613,808, filed on Feb. 4, 2015, now Pat. No. 9,089,580.

(30) Foreign Application Priority Data

May 23, 2014   (MX) .................. MX/A/2014/006259

(51) Int. Cl.
| | |
|---|---|
| *A61K 8/63* | (2006.01) |
| *A61K 8/36* | (2006.01) |
| *A61K 31/573* | (2006.01) |
| *A61K 8/64* | (2006.01) |
| *A61Q 7/00* | (2006.01) |
| *A61K 8/362* | (2006.01) |
| *A61K 8/67* | (2006.01) |
| *A61K 38/28* | (2006.01) |
| *A61K 45/06* | (2006.01) |

(52) U.S. Cl.
CPC .............. *A61K 31/573* (2013.01); *A61K 8/36* (2013.01); *A61K 8/362* (2013.01); *A61K 8/63* (2013.01); *A61K 8/64* (2013.01); *A61K 8/676* (2013.01); *A61K 38/28* (2013.01); *A61K 45/06* (2013.01); *A61Q 7/00* (2013.01)

(58) Field of Classification Search
CPC ................ C07J 1/00; C07J 3/00; C07J 5/00; A61K 8/63
See application file for complete search history.

(56) References Cited

U.S. PATENT DOCUMENTS

| | | | |
|---|---|---|---|
| 6,617,159 B1 | 9/2003 | Cancedda et al. | |
| 2003/0023228 A1* | 1/2003 | Parkinson | A61N 1/30 604/521 |
| 2005/0239722 A1* | 10/2005 | Albert | A61K 31/4709 514/28 |
| 2010/0172865 A1 | 7/2010 | Shantha et al. | |
| 2011/0212418 A1* | 9/2011 | Nakahara | A61L 27/3604 433/175 |

FOREIGN PATENT DOCUMENTS

WO    2010069519 A1    6/2010

OTHER PUBLICATIONS

Akorn-Strides, LLC, "Dexamethasone Sodium Phosphate Injection, USP", Section V: Labeling, 2006, pp. 1-21; obtained from www.fda.gov onOct. 13, 2015.*
Tambuwala et al., "Intralesional Corticosteroid Injection for Treatment of Central Giant-Cell Granuloma", Int. Journal of Contemporary Dentistry, 2011, pp. 140-144.*
Sigma-Aldrich, "Dexamethasone, Material Safety Data Sheet", 2015, pp. 1-8.*
Ximena Lopez, Mariana Castells, Alyne Ricker, Elsa F. Velazquez, Edward Mun, Allison B. Goldfine, Human Insulin Analog—Induced Lipoatrophy, Diabetes Care, 2008. 31:442-44.
R. Bruce Rutherford , Maria E. Ryan, James E. Kennedy, Marjorie M. Tucker, Marc F. Charette, Platelet-derived growth factor and dexamethasone combined with a collagen matrix induce regeneration of the periodontium in monkeys, Journal of Clinical Periodontology, 1993. 20:537-544.
Lorraine I. McKay, John A. Cidlowski, Corticosteroids in the Treatment of Neoplasms, Holland-Frei Cancer Medicine. 6th edition.Hamilton (ON): BC Decker; 2003 pp. 1-10. Editors: Kufe DW, Pollock RE, Weichselbaum RR, et al.

* cited by examiner

*Primary Examiner* — Lianko Garyu
(74) *Attorney, Agent, or Firm* — Benjamin Aaron Adler

(57) ABSTRACT

The present invention provides a formulation comprising a corticosteroid and an insulin analog or pharmaceutical compositions thereof. Also provided is a formulation comprising a corticosteroid, insulin lispro and at least one organic acid or pharmaceutical compositions thereof. The present invention provides methods for stimulating bone and/or cartilage growth, for treating tendon and/or ligament damage, for stimulating hair growth and/or reducing hair loss, for stimulating growth of a tooth and/or periodontium and for treating tumors and cysts of the jaw by administering the formulations described herein.

5 Claims, 25 Drawing Sheets

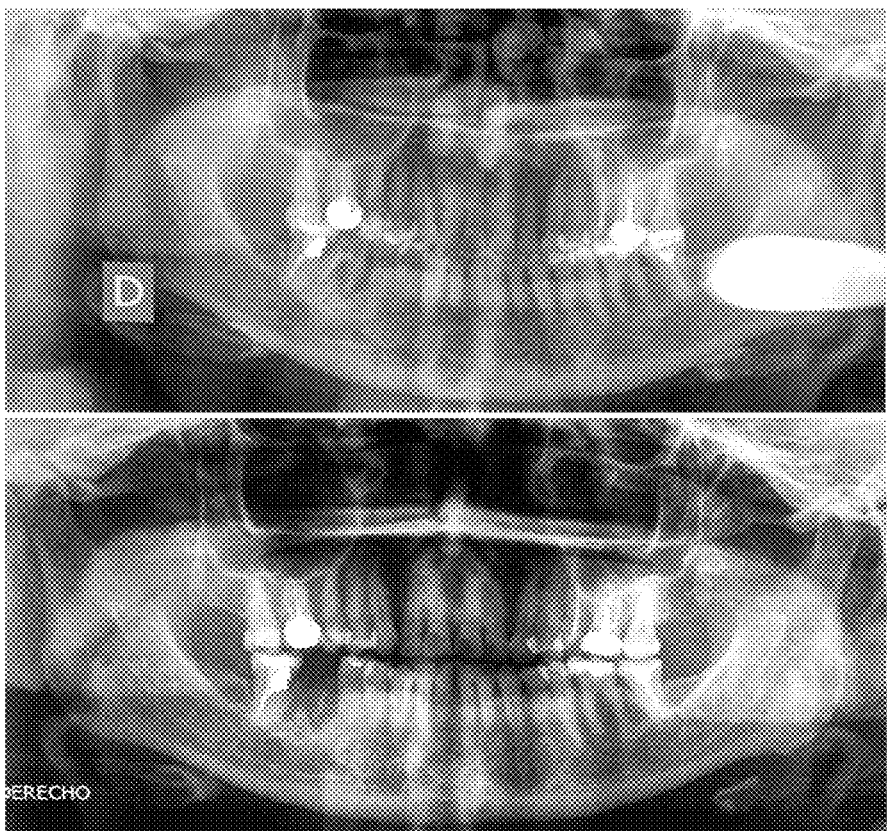
FIG. 3A
FIG. 3B
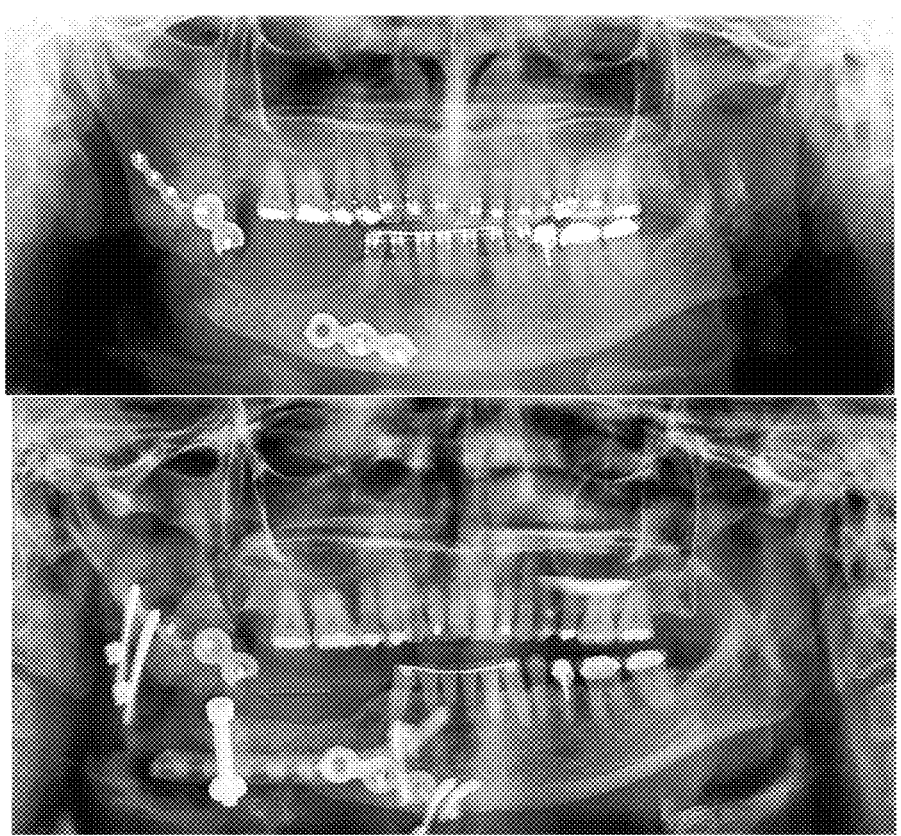
FIG. 4A
FIG. 4B

FIG. 7A
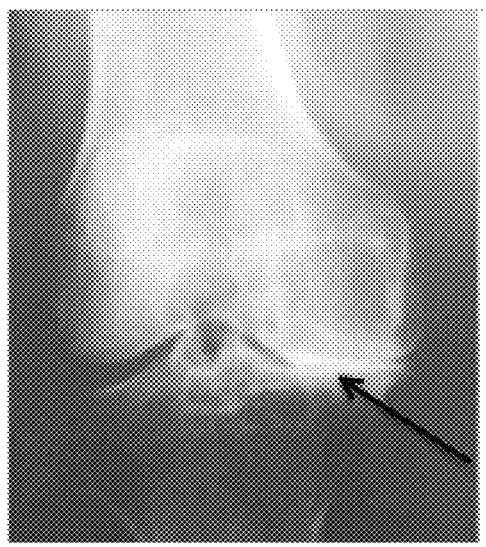 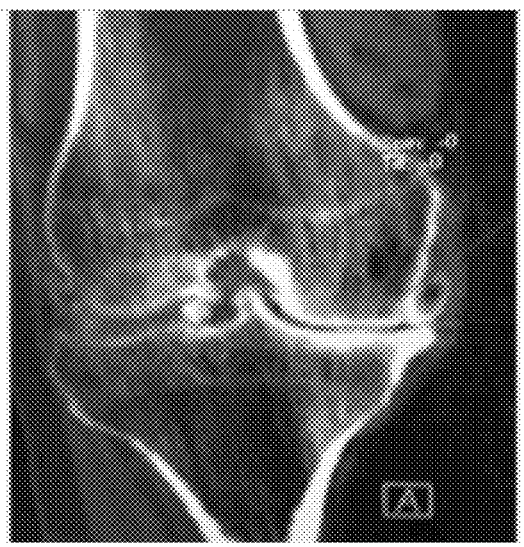
FIG. 7B        FIG. 7C

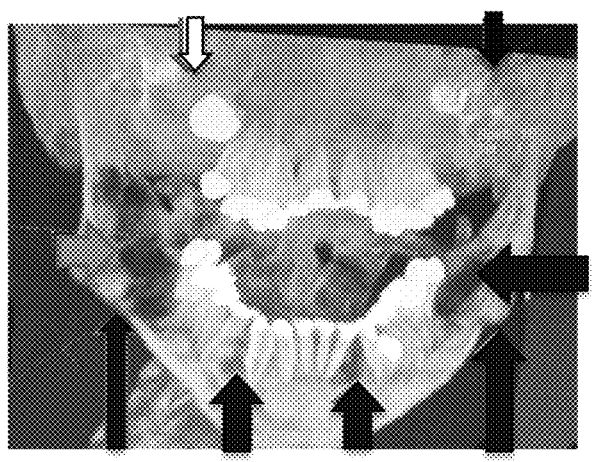
FIG. 10A FIG. 10B
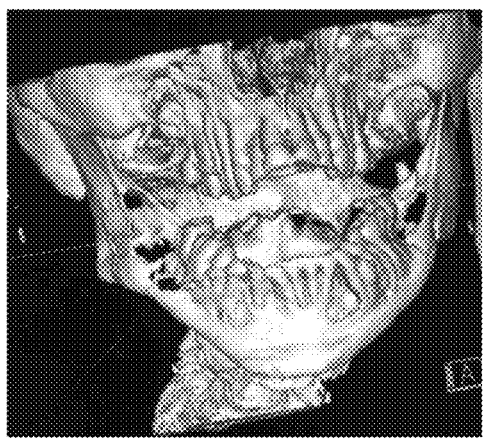
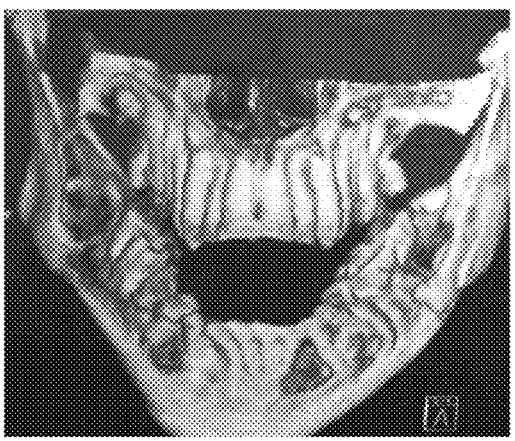
FIG. 10C FIG. 10D
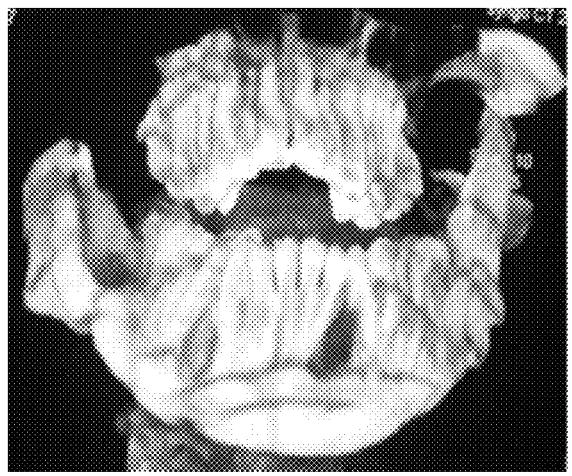
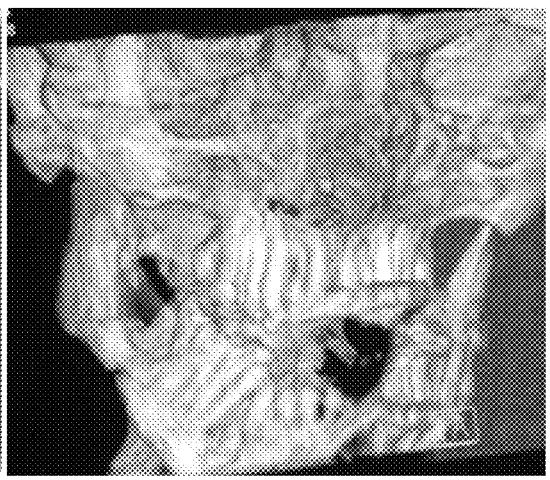
FIG. 10E FIG. 10F

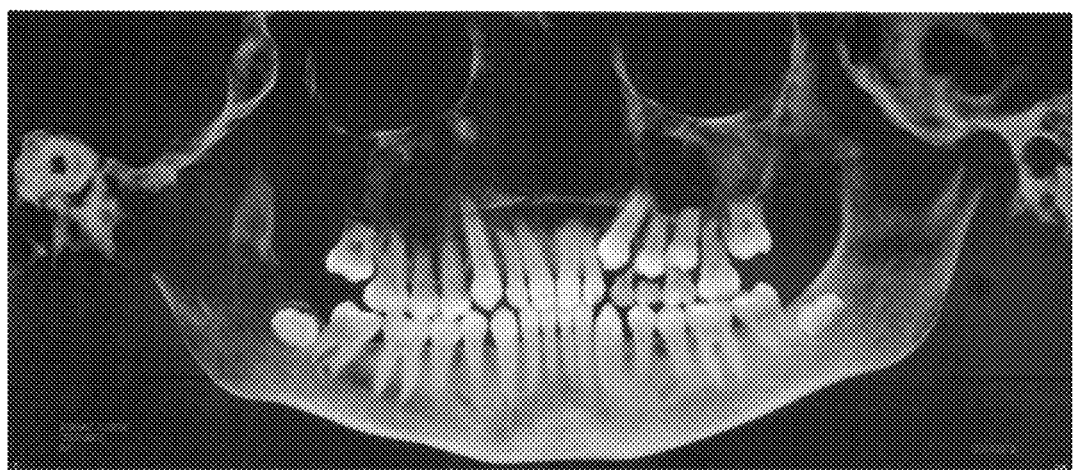
FIG. 15A
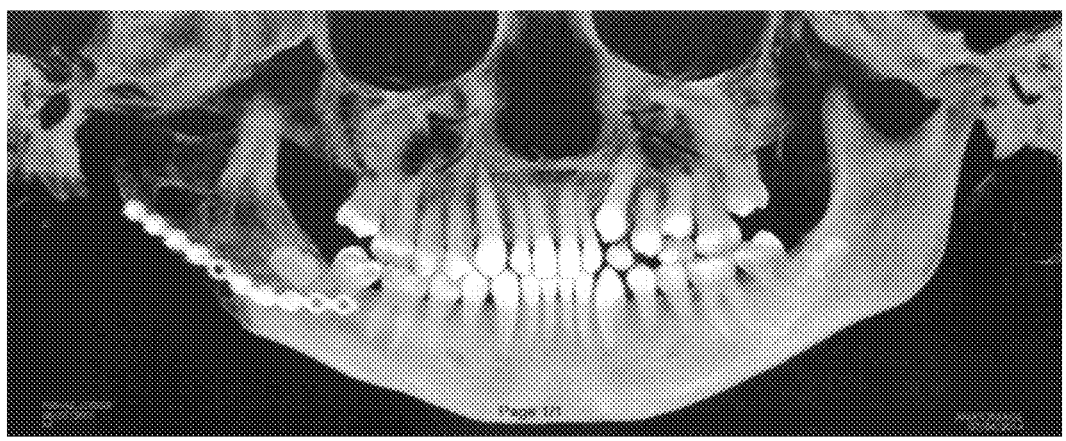
FIG. 15B
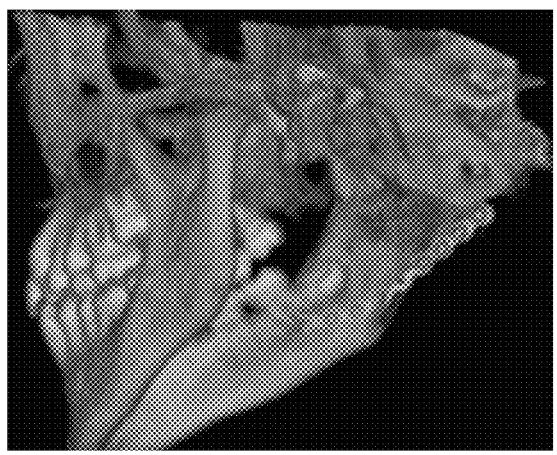 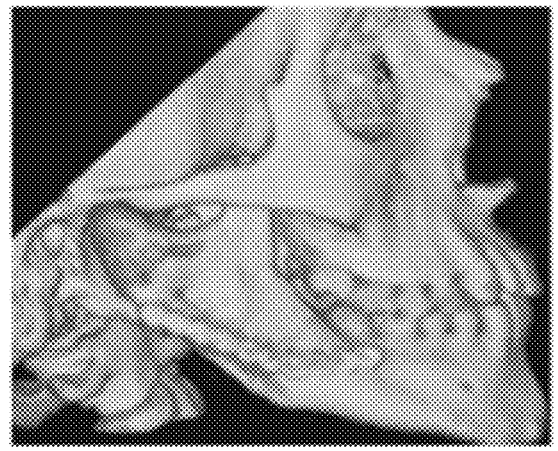
FIG. 15C              FIG. 15D

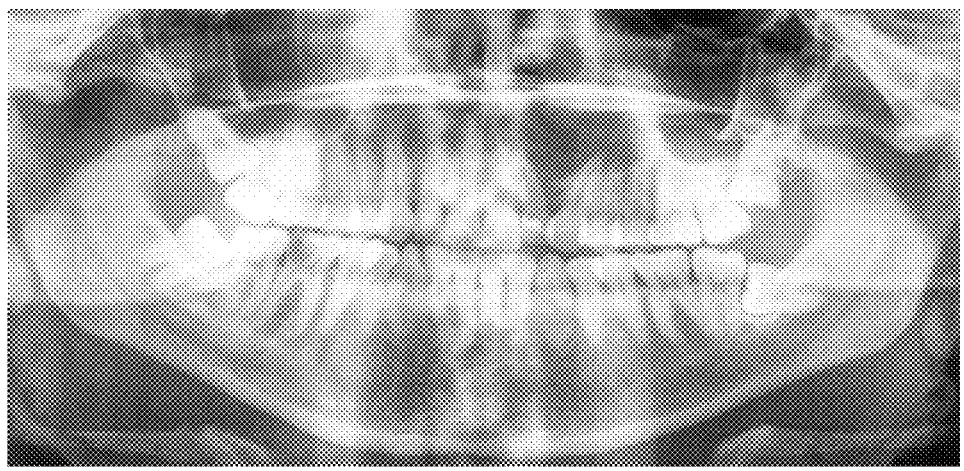
FIG. 17A
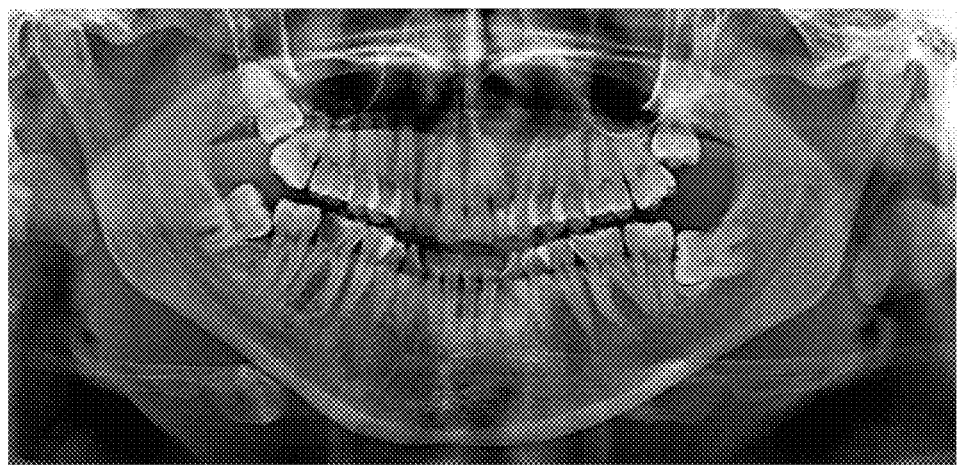
FIG. 17B
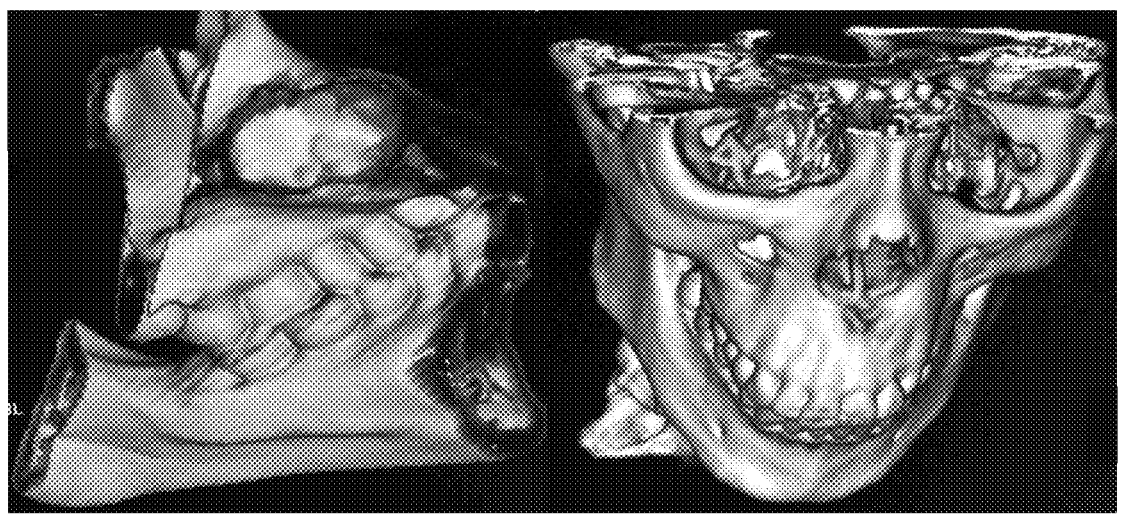
FIG. 17C    FIG. 17D

FORMULATION FOR REGENERATION OF BONE, CARTILAGE, TEETH, AND PERIODONTIUM AND TREATMENT OF TUMORS AND CYSTS

CROSS-REFERENCE TO RELATED APPLICATIONS

This is a continuation-in-part application under 35 U.S.C. §120 of pending international application PCT/US2015/032114, filed May 22, 2015, which claims benefit of priority under 35 U.S.C. §120 of pending application U.S. Ser. No. 14/613,808, filed Feb. 4, 2015, which claims benefit of priority under 35 U.S.C. §119(a) of pending Mexican application MX/2014/006259, filed May 23, 2014, the entirety of all of which are hereby incorporated by reference.

BACKGROUND OF THE INVENTION

1. Field of the Invention

The present invention relates generally to the fields of bone and cartilage physiology as well as the treatment of tumors and cysts. More specifically, the invention refers to the use of a formulation for the growth of bone and cartilage and the treatment of periodontium, tumors and cysts of the jaw and uses thereof.

2. Description of the Related Art

Osteoarthritis is a degenerative joint disease involving the symptomatic loss of cartilage in load-bearing areas of the joint and is frequently found in the temporomandibular joint, knee, hip, hand, foot and spine. Osteoarthritis causes significant pain and leads to disability and a decrease in the quality of life. Treatment includes orthotics and foot wear, physical therapy and exercise, gnathological dental prosthesis and occlusal plates (jaw), pharmacologic therapies such as hyaluronan derivatives and corticosteroids. Surgical management includes osteotomies, partial or total replacement of damaged articulation and autologous chondrocyte implantation, which can only provide a short-lived reduction in symptoms. Cartilage re-growth may be the ideal solution, but until now, is only used for small defects in specific areas of the femoral cartilage due to the expense and length of time required for cartilage re-growth. The cost of surgical treatments is very high and most of the time, the results do not meet expectations.

The basic management of long bone fractures involves its immobilization to ensure consolidation. Fracture repair could fail due to several reasons. For example, pseudarthrosis occurs when bone consolidation is not achieved after a bone fracture. It is caused by osteotomy or fracture instability, infection and/or loss of bone mass after comminuted fractures. Common treatments include physical therapy, pulsed electromagnetic field, medication with bisphosphonates, curettage of involved bone segments with or without bone graft and circular external fixation. Osteoporosis is a skeletal disorder characterized by compromised bone strength that increases the risk of fracture and also causes a delay in the consolidation of fractures. Current treatment includes the administration of bi- or polyphosphonates, that reduce bone resorption and bone turnover with side effects such as esophageal or gastric irritation, osteonecrosis of the jaw and atypical femoral fractures. Thus, new effective and non-harmful alternative treatments are needed.

The goals in treating midface fractures are to restore harmonious occlusion between the maxilla and mandible to obtain postoperative chewing function and reestablish midfacial height and facial symmetry. In midface and mandibular fractures, dental occlusion is the most important parameter in reestablishing facial contour and reduction of the fracture. Fracture of the alveolar process is a common injury and nearby soft tissues and teeth are often damaged. The aim of dentoalveolar fracture treatment is to re-establish the normal form and function of the masticatory system. Until now, the only treatment for compromised pulp and/or nerve of the teeth is a root canal, and in recurrent or more severe cases, dental extraction.

Tumors and cysts of the jaw are very common, have a high rate of recurrence, and are classified as odontogenic and non-odontogenic. Among the odontogenic cysts, follicular (dentigerous) cysts are particularly aggressive as they cause root resorption of adjacent teeth in more than 50% of cases. A follicular cyst is composed of a membranous sac or capsule that destroys adjacent bone tissue. Odontoma, a common odontogenic tumor, frequently interferes with teeth eruption.

Ameloblastoma is a benign but locally aggressive odontogenic tumor with high recurrence rates which can occur from the epithelial lining of a follicular cyst. The mandible is commonly affected including the ascending ramus, the premolar region and the anterior region, and some ameloblastomas are associated with an unerupted tooth. Ameloblastoma is observed as a radiolucent area presented in a multilocular or unilocular pattern and can be either completely radiolucent or radiolucent with septa. It causes extensive root resorption and displacement of teeth and has considerable potential for bone expansion. Surgical treatment may involve resection of the jaw or radiation therapy for inoperable tumors.

Non-odontogenic cysts include aneurysmal bone cysts and globulomaxillary cysts. The aneurysmal bone cyst is a rare benign lesion of the craniofacial bone which rapidly grows into a bony expansion. The globulomaxillary cyst is a fissural cyst which causes divergence of teeth roots. Treatment consists of surgical curettage or complete excision of the lesion.

The microenvironment of cysts and tumors has recently become a target for new treatments. The tumor's microenvironment is an integral part of its anatomy, physiology and functionality and is made of stem cells, soluble factors, signaling molecules, and extracellular matrix. Furthermore, the feasibility of differentiating stem cells into specialized cells or tissues by mechanical stimuli and/or chemical and biological substances has become evident, especially for tissue engineering applications.

Tissue engineering has the aim of inducing specific cell proliferation or to reprogram cells to heal or achieve tissue regeneration for clinical applications. Tissue engineering techniques include inductive tissue engineering (local delivery of growth factors to stimulate local cells and induce regeneration), conductive tissue engineering (use of a matrix or biomaterials to stimulate growth of existing tissue, cell transplantation (direct introduction of tissue previously manipulated in vitro, and hybrid tissue engineering (implantation of an in vitro "prepared" biomaterial within stem cells and growth factors).

Currently, there is no tissue engineering technique, formulation, or minimally invasive methodology or clinical procedure that works with the intralesional microenvironment to ensure even partial regeneration of injured bone, cartilage, teeth or periodontium or treatment of tumoral or cystic lesions of the jaw to promote regeneration of damaged tissues. Thus, the prior art is deficient in formulations and methods achieving these effects. The present invention fulfills this longstanding need and desire in the art.

SUMMARY OF THE INVENTION

The present invention is directed to a formulation comprising a corticosteroid and an insulin analog.

The present invention also is directed to a non-surgical and minimally invasive method for stimulating regeneration of injured bone in a subject. The method comprises the step of contacting injured bone with a formulation comprising a corticosteroid and an insulin analog.

The present invention is further directed to a non-surgical and minimally invasive method for stimulating regeneration of damaged cartilage in a subject. The method comprises the step of contacting injured cartilage with a formulation comprising a corticosteroid and an insulin analog.

The present invention is further directed to a non-surgical and minimally invasive method for stimulating regeneration of damaged ligaments and tendons in a subject. The method comprises the step of contacting injured ligaments or tendons with a formulation comprising a corticosteroid and an insulin analog.

The present invention is further directed to a non-surgical and minimally invasive method for stimulating hair growth and/or reducing hair loss in a subject. The method comprises the step of contacting a scalp with a formulation comprising a corticosteroid and an insulin analog.

The present invention is further directed to a non-surgical and minimally invasive method for treating dentoalveolar fractures and/or regeneration of teeth and/or periodontium in a subject. The method comprises the step of contacting damaged teeth and/or periodontium with a formulation comprising a corticosteroid and organic acids.

The present invention is further directed to a non-surgical and minimally invasive method for treating tumors and/or cysts of the jaw and/or regeneration of the damaged tissue in a subject. The method comprises the step of contacting tumors and/or cysts with a formulation comprising a corticosteroid and organic acids.

The present invention is further directed to a formulation comprising a corticosteroid, insulin lispro or a similarly fast acting insulin compound, and at least one organic acid.

The present invention is further directed to a formulation comprising a corticosteroid and at least one organic acid.

The present invention is further directed to a non-surgical and minimally invasive method for stimulating growth of hair and/or reducing hair loss in a subject in need of such treatment. The method comprises the step contacting scalp or desired tissue with a formulation comprising a corticosteroid and at least one organic acid.

Other and further aspects, features, benefits, and advantages of the present invention will be apparent from the following description of the presently preferred embodiments of the invention given for the purpose of disclosure.

BRIEF DESCRIPTION OF DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1A is an x-ray of the femur before treatment. FIG. 1B is an x-ray image of the femur fracture shown in FIG. 1A twenty days post-treatment. Osteogenesis in the middle of the fracture can be seen clearly.

FIG. 2A shows a panoramic x-ray of jaws with both a parasymphysis and a ramus fracture before treatment. FIG. 2B shows tomography twenty days post-treatment revealing consolidation of the pharasymphysis fracture shown in FIG. 2A. FIG. 2C shows tomography twenty days post-treatment revealing consolidation of the mandibular ramus fracture shown in FIG. 2A.

FIGS. 3A-3B are panoramic x-rays of a patient with exodontia and osteoporosis. FIG. 3A is the inferior first right molar tooth with an acute infection and submaxillary cellulitis by panoramic x-ray. Eosinophilic granuloma is seen in the mesial radicular area of the tooth. FIG. 3B is a panoramic x-ray ten days post-treatment of acute infection in the root fragments of the inferior first right molar tooth. Osteogenesis is seen around the extraction area, including low density regions due to osteoporosis.

FIGS. 4A-4B are panoramic x-rays of a fracture in the ascending ramus of the mandible of a patient with post-surgical osteomyelitis of 4 years. FIG. 4A is a panoramic x-ray of the injury after antiseptic disinfection and before application of the formulation of the present invention and placement of an external fixator. Notice the severe damage of the compact bone, the loss of continuity the structure of the bone and the broken reconstruction plates. FIG. 4B is a panoramic x-ray one month post-treatment and placement of an external fixator. Bone growth near the right fixator apex (arrow) can be seen clearly.

FIG. 5A is an x-ray of a coronal horizontal fracture with major loss of the clinical crown and an apical cyst with bone destruction, loss of periodontal ligament and rhizolysis before treatment. FIG. 5B is an x-ray seven days post-treatment showing osteogenesis. FIG. 5C is an x-ray fourteen days after the second treatment with the formulation of the present invention showing bone and periodontal ligament regeneration and treatment of the root resorption. Notice the treatment of the mesial root rhizolysis.

FIG. 6A is an x-ray of a patient with periodontal disease and root resorption before treatment. FIG. 6B is an x-ray fifteen days post-treatment showing regeneration of the damaged periodontal tissues and injured bone.

FIGS. 7A-7C are x-rays of a patient's left knee with Hallus Valgus arthropathy of 10 years. FIG. 7A is an x-ray of the left knee before treatment with the formulation of the present invention. FIGS. 7B-7C show an x-ray twenty-one days post-treatment of the left knee arthropahy. Notice the chondrogenesis (arrow) at the site of the injury in FIG. 7B.

FIG. 8A is an x-ray of coxarthrosis in the left hip before treatment. FIG. 8B is an x-ray of the left hip one month post-treatment with the formulation of the present invention showing chondrogenesis.

FIG. 9A shows tomography of a dentigerous cyst before treatment. FIG. 9B shows tomography of the cyst in the mandible before treatment. FIGS. 9C-9D show tomography seven days after the second treatment with the formulation of the present invention showing an external and internal view of osteogenesis. FIGS. 9E-9F shows tomography nine months post-treatment and five months after enucleation of the cyst capsule and extraction of the non-erupted tooth showing osteogenesis of the cortical and cancellous bone.

FIGS. 10A-10F are tomographies of a patient with Gorlin Goltz syndrome and multiple pathologies. FIG. 10A shows tomography of the bilateral mandibular fracture, keratocystic odontogenic tumors, compound and complex odontomas and dentigerous cyst. FIGS. 10B-10D show tomography of consolidation of both fractures in the mandible six days after treatment with the present formulation. Bone growth in the cystic lesions can be seen clearly. FIGS. 10E-10F shows tomography five months post-treatment with the present formulation of the bilateral mandibular fracture, keratocystic odontogenic tumors, compound and complex odontomas, and dentigerous cyst. Osteogenesis on the right side of the mandible and full treatment of the fractures, dentigerous cyst, left keratocystic odontogenic tumor, and complex and compound odontomas.

FIG. 11A shows radiography of the keratocystic tumor before treatment with the formulation of the present invention. FIGS. 11B-11C show radiography seven days post-treatment showing growth of the normal mandibular trabecula along with an increase of bone density. The osteogenesis of healthy trabecular bone and is denoted by the arrows and can be seen clearly. FIG. 11D shows tomography of an injured mandible three months after treatment. Growth of mandibular trabecula is observed along with an increase of bone density. Notice the reduction in the hypercalcified regions.

FIG. 12A is an x-ray before treatment with the formulation of the present invention. Notice the recurrence on previously resected bone, including dental organs. FIGS. 12B-12C show an x-ray seven days post-treatment showing neoformation of bony bridges due to osteogenesis. FIG. 12D is an x-ray fourteen days post-treatment showing poor osteogenesis and an extended capsule along the whole lesion, filled with intralesional fluid. Note the appearance of osseous tissue and structures inside the capsule. FIG. 12E shows tomography one month after capsule enucleation and the third application of the present formulation. Notice the filling of the empty trabecular and compact bone niches due to a quick and efficient osteogenesis. FIGS. 12F-12G show tomography 120 days after the third application of the present formulation showing remarkable osteogenesis.

FIG. 13A is a panoramic x-ray showing dentoid structure within the well formed cystic capsule, before treatment with the formulation of the present invention. FIG. 13B is a periapical x-ray seven days post-treatment showing resorption of the cystic capsule along with formation of normal healthy cancellous bone within the injured area.

FIG. 14A is a panoramic x-ray of the injury before treatment with the formulation of the present invention. FIG. 14B shows tomography of the right mandibular lingual view of the lesion before treatment with the formulation of the present invention. FIG. 14C shows tomography three days post-treatment showing cortical bone regeneration. FIGS. 14D-14E show tomographies three days post-treatment showing regeneration of the external cortical and cancellous bone. FIGS. 14F-14G show tomography ninety days post-treatment showing treatment of the tumor.

FIGS. 15A-15D are tomographies of a recurrent mandibular aneurysmal bone cyst. FIG. 15A is an x-ray showing bone lysis of the mandibular condyle and a multilocular lesion in the right ascending ramus. FIG. 15B is an x-ray before treatment with the formulation of the present invention showing a multilocular recurrent lesion and titanium miniplate with screws from an advanced osteotomy. FIGS. 15C-15D is an x-ray seven days post-treatment showing almost complete osteogenesis at the site of the bone cyst.

FIG. 16A shows tomography of a fibroma, dental migration and characteristic bulkiness of the external bone, hyperdense bone areas with calcifying nodules and low density regions with fluid filled loculi. FIGS. 16B-16C show tomographies of cortical bone bulkiness before treatment with the formulation of the present invention. FIG. 16D shows tomography nine days post-treatment showing osteogenesis in the loculi. FIGS. 16E-16F show tomographies thirty five days post-treatment showing a decrease of bulkiness of the cortical bone.

FIGS. 17A-17D are x-rays of a globule maxillary cyst in the left side of the premaxilla. FIG. 17A is a panoramic x-ray, before treatment with the formulation of the present invention, showing a low density region and extended root displacement which extended to the right side across the base of the nasal septum. FIG. 17B is an x-ray thirty-five days post-treatment showing osteogenesis within the cystic lesion in the premaxilla. FIGS. 17C-17D is an x-ray sixty-five days post-treatment showing osteogenesis of the cancellous and compact bone in the cystic lesion in the premaxilla.

FIG. 18A is an x-ray before treatment with the formulation of present invention showing part of the cystic lesion, labeled with a cross. FIG. 18B is an x-ray one month post-treatment showing new bone formation (arrows) within the original cystic lesion in tooth 13.

FIG. 19A shows stem cells isolated from dental pulp. Notice the fibroblastoid morphology. FIG. 19B shows stem cells isolated from the intralesional content of an ameloblastoma. Notice the fibroblastoid morphology. FIG. 19C shows stem cells isolated from an ameloblastoma and treated with one of the formulations of the present invention. Induced proliferation in comparison with the control can be seen. FIG. 19D shows stem cells isolated from an ameloblastoma and treated with a different formulation of the present invention. A change in the cellular lineage can be seen. FIG. 19E shows control stem cells, isolated from an ameloblastoma and without treatment with a formulation of the present invention. Notice the fibroblastoid morphology.

FIG. 22A shows the initial tomography with an axial cut showing the septal fistula.

FIG. 22B is a tomography with an axial cut showing the fistula seven days post-treatment with a defect length of 8.103 mm. FIG. 22C is a tomography with an axial cut showing the fistula fifteen days post-treatment with a defect length of 4.269 mm which is a 50% reduction in length. FIGS. 22D-22E are 3D tomographies of reconstruction showing formation of cartilage bridges and recovery of the septum's anatomy.

FIG. 23A is the tomography showing different angles of a traumatic arthropathy of the right knee. FIG. 23B is the tomography showing cartilage regeneration 3 weeks after the treatment. FIG. 23C is the tomography showing cartilage, bone and ligament's regeneration 90 days after the treatment.

DETAILED DESCRIPTION OF THE INVENTION

Figure 1A:
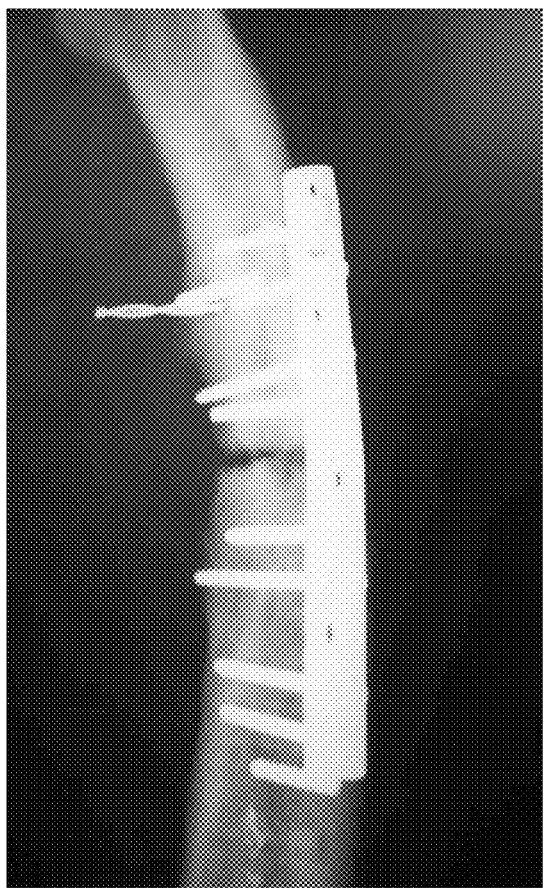
FIGS. 1A-1B are x-ray images of an atrophic femoral pseudoarthrosis lesion that developed over 13 years.

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "regeneration" is defined as at least partial osteogenesis and/or chondrogenesis observed, e.g., by imaging and/or x-ray medical techniques as would be readily recognized by a person having ordinary skill in this art.

As used herein, the term "teeth" or "tooth" is defined as dentin, cementum and pulp and excludes enamel.

In one embodiment of the present invention, there is provided a formulation, comprising a corticosteroid and an insulin analog. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation in an amount of from about 0.5 mg/mL to about 10 mg/mL. A representative example of a useful insulin analog is a fast-acting insulin analog. Preferably, the fast-acting insulin analog is insulin lispro, insulin aspart or insulin glulisine. As a representative example, the insulin lispro may be contained in the formulation in an amount of from about 0.000115 µg/mL to about 0.00345 µg/mL. Typically, the formulation is dissolved in a vehicle. Representative examples of useful vehicles include but are not limited to normal saline, phosphate buffered saline or water for injection. In one preferred aspect, the formulation further comprises at least one organic acid. Representative examples of useful organic acids include but are not limited to citric acid, ascorbic acid, malic acid and lactic acid. Generally, such organic acids are contained in the formulation in an amount of from about 0.05 mg/mL to about 5 mg/mL. As is well known in the art, the formulation of the present invention may be formulated in a variety of forms as pharmaceutical compositions or formulations. Representative examples of pharmaceutical forms include but are not limited to a suspension, spray, solution, nose drops, gel, paste, ointment, cream, nanoparticle, liposome, microcapsule, delivery device or powder.

In another embodiment of the present invention, there is provided a non-surgical and minimally invasive method for stimulating growth or regeneration of bone in a subject, comprising, the steps of contacting the bone with a formulation comprising a corticosteroid and an insulin analog, and working within the intralesional microenvironment. Preferably, the growth or regeneration of the bone occurs within a period of time of 1 to 6 weeks. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or pharmaceutical or medical composition thereof in an amount of from about 0.5 mg/mL to about 10 mg/mL. A representative example of a useful insulin analog is a fast-acting insulin analog. Preferably, the fast-acting insulin analog is insulin lispro. For example, the insulin lispro may be contained in the formulation in an amount of from about 0.000115 µg/mL to about 0.00345 µg/mL. Alternatively, the fast-acting insulin analog may be insulin aspart or insulin glulisine. Typically, the formulation is dissolved in a vehicle. Representative examples of useful vehicles include but are not limited to normal saline, phosphate buffered saline or water for injection. In one preferred aspect, the formulation further comprises at least one organic acid. Representative examples of useful organic acids include but are not limited to citric acid, ascorbic acid, malic acid and lactic acid. Generally, such organic acids are contained in the formulation or pharmaceutical or medical composition thereof in an amount of from about 0.05 mg/mL to about 5 mg/mL. As is well known in the art, this method may be accomplished using a pharmaceutical composition of the formulation of the present invention in a form desirable for this specific method. As would be readily recognized by a person having ordinary skill in this art, this method may be applied to stimulate regeneration of a wide variety of bone or bone-like tissue injuries. Representative examples of bone or bone-like tissue injuries which may be stimulated to regenerate include but are not limited to bone fractures, bone fissures, bone resorption, bone necrosis, osteoporosis and pseudoarthrosis.

In yet another embodiment of the present invention, there is provided a non-surgical and minimally invasive method for stimulating the regeneration of damaged cartilage in a subject, comprising the step of contacting the injured cartilage with a formulation comprising a corticosteroid and insulin analog, and working with the intralesional microenvironment. Preferably, the regeneration of damaged cartilage is stimulated within a period of time of 1 to 4 weeks. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or pharmaceutical or medical composition thereof in an amount of from about 0.5 mg/mL to about 10 mg/mL. A representative example of a useful insulin analog is a fast-acting insulin analog. Preferably, the fast-acting insulin analog is insulin lispro. For example, the insulin lispro may be contained in the formulation or pharmaceutical or medical composition thereof in an amount of from about 0.000115 μg/mL to about 0.00345 μg/mL. Alternatively, the fast-acting insulin analog may be insulin aspart or insulin glulisine. Typically, the formulation is dissolved in a vehicle. Representative examples of useful vehicles include but are not limited to normal saline, phosphate buffered saline or water for injection. In one preferred aspect, the formulation further comprises at least one organic acid. Representative examples of useful organic acids include but are not limited to citric acid, ascorbic acid, malic acid and lactic acid. Generally, such organic acids are contained in the formulation or pharmaceutical or medical composition thereof in an amount of from about 0.05 mg/mL to about 5 mg/mL. As is well known in the art, this method may be accomplished using a pharmaceutical composition of the formulation of the present invention in a form desirable for this specific method. As would be readily recognized by a person having ordinary skill in this art, this method may be applied to stimulate regeneration of a wide variety of cartilage injuries. Representative examples of cartilage injuries include but are not limited to arthropathies of the temporomandibular joint, acromioclavicular joint, elbow joint, wrist joint, glenohumeral joint, knee joint, coxofemoral joint, meniscal tears, or a fistula occurring abnormally or as a result of a surgical procedure.

In yet another embodiment of the present invention, there is provided a non-surgical and minimally invasive method for stimulating growth of hair and/or reducing hair loss in a subject, comprising the step contacting scalp with a formulation comprising a corticosteroid and an insulin analog. Typically, the growth of hair is seen within a period of about 7 to 15 days. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or pharmaceutical or medical composition thereof in an amount of from about 0.5 mg/mL to about 10 mg/mL. Typically, the formulation is dissolved in a vehicle. Representative examples of useful vehicles include but are not limited to normal saline, phosphate buffered saline or water for injection. A representative example of a useful insulin analog is a fast-acting insulin analog. Preferably, the fast-acting insulin analog is insulin lispro. For example, the insulin lispro may be contained in the formulation or pharmaceutical or medical composition thereof in an amount of from about 0.000115 μg/mL to about 0.00345 μg/mL. Alternatively, the fast-acting insulin analog may be insulin aspart or insulin glulisine. In one preferred aspect, the formulation further comprises at least one organic acid. Representative examples of useful organic acids include but are not limited to citric acid, ascorbic acid, malic acid and lactic acid. Generally, such organic acids are contained in the formulation or pharmaceutical or medical composition thereof in an amount of from about 0.05 mg/mL to about 5 mg/mL. As is well known in the art, this method may be accomplished using a pharmaceutical composition of the formulation of the present invention in a form desirable for this specific method. As would be readily recognized by a person having ordinary skill in this art, this method may be used to treat a wide variety of conditions related with hair loss. Representative examples of conditions related with hair loss which may be treated using this method include but are not limited to alopecia, such as partial alopecia or hormonal alopecia.

In yet another embodiment of the present invention, there is provided a non-surgical and minimally invasive method for treating arthropathy. This method comprises the step of contacting a joint having arthropathy with a formulation comprising a corticosteroid and an insulin analog. Preferably, the growth of the bone and cartilage is seen within a period of 21 days to 90 days. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or pharmaceutical or medical composition thereof in an amount of from about 0.5 mg/mL to about 10 mg/mL. Representative examples of useful insulin analog includes but is not limited to insulin lispro. Alternatively, the fast-acting insulin analog may be insulin aspart or insulin glulisine. The insulin lispro may be contained in the formulation or pharmaceutical or medical composition thereof in an amount of from about 0.000115 μg/mL to about 0.00345 μg/mL. In this embodiment, the formulation may contain at least one organic acid. The representative examples of the organic acid include but are not limited to citric acid, ascorbic acid, malic acid or lactic acid. In a preferred embodiment, the concentration of the organic acid in the formulation is from about 0.05 mg/mL to about 5 mg/mL.

In yet another embodiment of the present invention, there is provided a non-surgical and minimally invasive method for treating injuries of ligaments and tendons. This method comprises the step of contacting the damaged tendon or ligament with a formulation comprising a corticosteroid and an insulin analog. Preferably, the regeneration of tendons or ligaments is seen within a period of 7 days to 90 days. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or pharmaceutical or medical composition thereof in an amount of from about 0.5 mg/mL to about 10 mg/mL. A representative example of useful insulin analog includes but is not limited to insulin lispro. Alternatively, the fast-acting insulin analog may be insulin aspart or insulin glulisine. The insulin lispro may be contained in the formulation or pharmaceutical or medical composition thereof in an amount of from about 0.000115 μg/mL to about 0.00345 μg/mL. A person having average ability, in view of the teaching of the present invention, would be readily able to define useful dosages of insulin aspart or insulin glulisine. Typically, the composition is dissolved in a vehicle. Representative examples of useful vehicles include but are not limited to normal saline, phosphate buffered saline or water for injection. In one preferred aspect, the formulation further comprises at least one organic acid. Representative examples of useful organic acids include but are not limited to citric acid, ascorbic acid, malic acid and lactic acid. Generally, such organic acids are contained in the formulation or pharmaceutical or medical composition thereof in an amount of from about 0.05 mg/mL to about 5 mg/mL. As is well known in the art, this method may be accomplished using a pharmaceutical composition of the formulation of the present invention in a form desirable for this specific method. As would be readily recognized by a person having ordinary skill in this art, this method may be applied to stimulate regeneration of a wide variety of ligament and tendon injuries. Representative examples of ligament and tendon injuries include but are not limited to enthesitis, tears, sprains and total or partial ruptures.

In yet another embodiment of the present invention, there is provided a non-surgical and minimally invasive method for treating dentoalveolar fractures and/or regeneration of teeth and/or periodontium in a subject, comprising the step of contacting the damaged dental organ and/or related periodontal tissues with a formulation comprising a corticosteroid and organic acids, and working with the intralesional microenvironment. Preferably, the beneficial treatment of dentoalveolar fractures and/or regeneration of teeth and/or periodontium is seen within a period of time of 1 to 2 weeks. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or medical or pharmaceutical composition thereof in an amount of from about 0.5 mg/mL to about 10 mg/mL. A representative example of a useful insulin analog is a fast-acting insulin analog. Preferably, the fast-acting insulin analog is insulin lispro. For example, the insulin lispro may be contained in the formulation or pharmaceutical or medical composition thereof in an amount of from about 0.000115 µg/mL to about 0.00345 µg/mL. Alternatively, the fast-acting insulin analog may be insulin aspart or insulin glulisine. Typically, the formulation is dissolved in a vehicle. Representative examples of useful vehicles include but are not limited to normal saline, phosphate buffered saline or water for injection. In one preferred aspect, the formulation further comprises at least one organic acid. Representative examples of useful organic acids include but are not limited to citric acid, ascorbic acid, malic acid and lactic acid. Generally, such organic acids are contained in the formulation or pharmaceutical or medical composition thereof in an amount of from about 0.05 mg/mL to about 5 mg/mL. As is well known in the art, this method may be accomplished using a pharmaceutical composition of the formulation of the present invention in a form desirable for this specific method. As would be readily recognized by a person having ordinary skill in this art, this method may be applied to stimulate the regeneration of a wide variety of injuries in dental organs and related periodontal tissues. Representative examples of injuries and tissues include but are not limited to, dentoalveolar fractures, root and alveolar bone resorption, rhizolysis, tooth mobility, degradation of dentin, cementum, periodontal ligament, pulp, alveolar bone, gingiva and nerve.

In yet another embodiment of the present invention, there is provided a non-surgical and minimally invasive method for treating tumors and/or cysts of the jaw and regeneration of damaged tissues, comprising the step of contacting tumors and/or cysts with a formulation comprising a corticosteroid and organic acids. Preferably, the beneficial treatment of tumors and/or cysts of the jaw and regeneration of damaged tissues is seen within a period of 3 to 15 days. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or pharmaceutical or medical composition thereof in an amount of from about 0.5 mg/mL to about 10 mg/mL. Typically, the formulation is dissolved in a vehicle. Representative examples of useful vehicles include but are not limited to normal saline, phosphate buffered saline or water for injection. Representative examples of useful organic acids include but are not limited to citric acid, ascorbic acid, malic acid and lactic acid. Generally, such organic acids are contained in the formulation or pharmaceutical or medical composition thereof in an amount of from about 0.05 mg/mL to about 5 mg/mL. As is well known in the art, this method may be accomplished using a pharmaceutical composition of the formulation of the present invention in a form desirable for this specific method. As would be readily recognized by a person having ordinary skill in this art, this method may be used to treat a wide variety of tumors and/or cysts of the jaw. Representative examples of tumors and/or cysts which may be treated using this method include but are not limited to follicular cysts, keratocystic odontogenic tumors with and without calcifying regions, odontomas, ameloblastomas, Gorlin's tumors, apical cysts, aneurismal bone cysts, ossifying fibromas and globulomaxillary nasolabial cysts. As would be readily recognized by a person having ordinary skill in this art, this method may be used to regenerate a wide variety of damaged tissues caused by tumors and/or cysts of the jaw. Representative examples of tissues which may be regenerated using this method include but are not limited to cancellous and compact bone, nerves, gingiva, dentin, cementum, periodontal ligament, pulp, alveolar bone, muscle and cartilage.

In yet another embodiment of the present invention, there is provided a non-surgical and minimally invasive method for stimulating growth of hair and/or reducing hair loss in a subject in need of such treatment, comprising the step contacting scalp with a formulation comprising a corticosteroid and at least one organic acid. Preferably, the growth of hair is seen within a period of about 7 to 15 days. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or pharmaceutical or medical composition thereof in an amount of from about 0.5 mg/mL to about 10 mg/mL. Typically, the formulation is dissolved in a vehicle. Representative examples of useful vehicles include but are not limited to normal saline, phosphate buffered saline or water for injection. Representative examples of useful organic acids include but are not limited to citric acid, ascorbic acid, malic acid and lactic acid. Generally, such organic acids are contained in the formulation or pharmaceutical or medical composition thereof in an amount of from about 0.05 mg/mL to about 5 mg/mL. As is well known in the art, this method may be accomplished using a pharmaceutical composition of the formulation of the present invention in a form desirable for this specific method. As would be readily recognized by a person having ordinary skill in this art, this method may be used to treat a wide variety of conditions related with hair loss. Representative examples of conditions related with hair loss which may be treated using this method include but are not limited to alopecia, such as partial alopecia or hormonal alopecia.

In another embodiment of the present invention, there is provided a formulation, referred to herein as formulation 1, comprising a corticosteroid and at least one organic acid. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or pharmaceutical or medical composition thereof in an amount of from about 0.5 mg/mL to about 10 mg/mL. Typically, the formulation is dissolved in a vehicle. Representative examples of useful vehicles include but are not limited to normal saline, phosphate buffered saline or water for injection. Representative examples of useful organic acids include but are not limited to citric acid, ascorbic acid, malic acid and lactic acid. Generally, such organic acids are contained in the formulation or pharmaceutical or medical composition thereof in an amount of from about 0.05 mg/mL to about 5 mg/mL. As is well known in the art, the formulation of the present invention may be formulated in a variety of forms as pharmaceutical compositions. Representative examples of pharmaceutical forms include but are not limited to a suspension, spray, nose drops, solution, gel, paste, ointment, cream, nanoparticle, liposome, microcapsule, delivery device or powder.

In yet another embodiment of the present invention, there is provided a formulation, referred to herein as formulation 2, comprising a corticosteroid; insulin lispro; and at least one organic acid. Representative examples of useful corticosteroids include but are not limited to dexamethasone, cortisol, prednisone, prednisolone, methylprednisolone, betamethasone, triamcinolone, beclometasone, fludrocortisone acetate or deoxycorticosterone acetate. In one preferred embodiment, the corticosteroid is dexamethasone. For example, the dexamethasone may be contained in the formulation or pharmaceutical or medical composition thereof in an amount of from about 0.5 mg/mL to about 10 mg/mL. A representative example of a useful insulin analog is a fast-acting insulin analog. Preferably, the fast-acting insulin analog is insulin lispro. For example, the insulin lispro may be contained in the formulation or pharmaceutical or medical composition thereof in an amount of from about 0.000115 µg/mL to about 0.00345 µg/mL. Alternatively, the fast-acting insulin analog may be insulin aspart or insulin glulisine. A person having average ability, in view of the teaching of the present invention, would be readily able to define useful dosages of insulin aspart or insulin glulisine. Typically, the formulation is dissolved in a vehicle. Representative examples of useful vehicles include but are not limited to normal saline, phosphate buffered saline or water for injection. In one preferred aspect, the formulation further comprises at least one organic acid. Representative examples of useful organic acids include but are not limited to citric acid, ascorbic acid, malic acid and lactic acid. Generally, such organic acids are contained in the formulation or pharmaceutical or medical composition thereof in an amount of from about 0.05 mg/mL to about 5 mg/mL. As is well known in the art, the formulation of the present invention may be formulated in a variety of forms as pharmaceutical compositions. Representative examples of pharmaceutical forms include but are not limited to a suspension, spray, solution, nose drops, gel, paste, ointment, cream, nanoparticle, liposome, microcapsule, delivery device or powder.

As is well known in the art, the compositions and formulations of the present invention may be applied or administered in a wide variety of therapeutically effective forms and techniques. In a preferred embodiment, the formulations of the present invention are administered or applied intralesionally or directly into the injury niche, in order to work with the content of the microenvironment of the lesion, including stem cells. For example, the formulation of the present invention may be applied intralesionally into the periosteal and endosteal injured region for the treatment of bone fractures and osteoporosis. In another embodiment, the formulation of the present invention may be applied intralesionally into the niche of the damaged cartilage for arthropathy of the temporomandibular joint, the acromioclavicular joint, the elbow joint, the wrist joint, the glenohumeral joint, the knee or for coxarthrosis, or a nasal fistula. In another embodiment, the formulation of the present invention may be applied intralesionally into the niche of injured tendons or ligaments. In another embodiment, the formulation of the present invention may be applied intralesionally and peripherally to compromised teeth and/or compromised periodontal tissues for its treatment and/or regeneration. In yet another embodiment, the formulation of the present invention may be applied intralesionally into the tumors or cysts of the jaw for its treatment and regeneration of damaged tissues. In another embodiment, the formulation of the present invention may be applied intradermally into the scalp for the treatment of, for example, alopecia such as partial alopecia or hormonal alopecia.

As is well known in the art, the compositions and formulations of the present invention may be applied or administered to either human or non-human subjects.

As is well known in the art, the compositions and formulations of the present invention may be applied or administered alone or in combination with one or more other therapeutic agents, to a subject to treat a particular condition.

The following examples are given for the purpose of illustrating various embodiments of the invention and are not meant to limit the present invention in any fashion.

EXAMPLE 1

Treatment Method for Cysts and Tumors of the Jaw

When present, most of the intralesional fluid is drained. If clinical evidence of infection is found inside the lesion, the niche is washed. Depending on the size of the injury, from 1-8 mL of an antiseptic (electrolyzed superoxidized water solution of neutral pH, ESTERICIDE®) is injected and immediately drained back. Formulation 1 of the present invention is applied, intralesionally and percutaneously, perfusing all loculi, making sure to reach all perimeter walls of the lesion, according to the tomography, and, if necessary, a fluoroscope is used. Depending on the tumor's size, 0.5-5.0 mL of the formulation may be perfused. The progress of the treatment is clinically monitored every 3 or 5 days, any intralesional fluid is aspirated with a needle, and tomographic follow-up is given one and two weeks post-treatment.

Three cases may arise. First, if the osteogenesis progressed satisfactorily, clinical follow-up is continued weekly with a monthly tomography (during the first two months and tomography is performed every three months), until observing treatment of the lesion. Second, if the osteogenesis stops completely or slowly progresses, with or without formation of intralesional fluid, then the intralesional fluid is aspirated with a needle, if formed, and a second application of the present formulation is performed. The patient is monitored every 3 or 5 days along with aspiration of any intralesional liquid with a needle, if formed, and a monthly tomography (during the first two months and then the tomography is performed every three months) until the lesion has been completely resolved. Third, if bone resorption occurs with or without formation of a cystic or tumoral capsule with or without intralesional liquid, then enucleation of the capsule is performed and/or curettage of the injury under local anesthesia, the wound is closed and the formulation of the present invention is applied. The patient is monitored every 3 or 5 days with aspiration of any intralesional liquid, if formed, and monthly tomography is performed (during the first two months and then the tomography is performed every three months) until the lesion has completely resolved. In all cases, after observing treatment of the injury, clinical monitoring is continued in accordance with the regulations for this type of pathology.

EXAMPLE 2

Treatment Method for Regeneration of Teeth and Periodontium

Dental cleaning (scaling) is performed using ESTERICIDE® antiseptic as the irrigant. In the case of periodontal disease or infection, an antiseptic (ESTERICIDE®) is perfused intralesionally and peripheral to the compromised tooth, once a day until eradication of the infection. In case of tooth decay, cavity, dental crack, loose filling or pulp exposure, the injury is treated first. When major loss of dental tissue has occurred, significant mobility may be present, so ferulization might be required. Peripheral immobilization with surgical wire could be necessary when treating a coronal and/or apical fractured tooth. Application of sodium fluoride is recommended when treating a fracture involving presence of enamel. Approximately 0.5-3.0 mL of formulation 1 of the present invention was applied peri- and intraligamentary.

EXAMPLE 3

Treatment Method for Bone Fractures and Osteoporosis

If required, the injury is pretreated as follows. In the case of osteomyelitis, 1-5 mL of antiseptic (ESTERICIDE®) is perfused intralesionally, every three days for six weeks. Formulation 2 of the present invention is applied after three days. For facial fractures without infection, 0.5-4 mL of antiseptic (ESTERICIDE®) is perfused intralesionally in the fracture bed. For mandibular or long bone fractures, an external fixator is placed adjusting to the correct position of the bone segments. In all cases, 0.5-5.0 mL of the formulation of the present invention is applied intralesionally into the periosteal and endosteal region, perfusing into cancellous bone.

EXAMPLE 4

Treatment Method for Regeneration of Cartilage for Arthropathy of Temporomandibular Joint Local nerve block anesthesia is performed with antisepsis. To identify the puncture site, an imaginary line of 2 cm is drawn from the ear's tragus to the eye's lateral canthus and then a perpendicular line of 1 cm is drawn from that point to the angle of mandible. After ensuring the correct puncture location, 2 mL of formulation 2 of the present invention was perfused. A protective dressing of ESTERICIDE® gel is applied over puncture site. A second application of the present formulation is administered one month post-treatment with radiographic and tomographic monitoring of the lesion.

EXAMPLE 5

Treatment Method for Regeneration of Cartilage for Arthropathy of Acromioclavicular Joint The patient's hands are placed to rest over her/his lap remaining still without moving arms or shoulders, and looking to the opposite direction of the injured joint. Antisepsis and intramuscular infiltration of lidocaine (2%) is performed. The skin entry site is just above the acromioclavicular joint. To locate it, the clavicular line is followed from the medial to lateral position and the joint is in a small depression zone that presents sensitivity in the case of an injury. After ensuring the correct puncture location, 2 mL of formulation 2 of the present invention is perfused. A protective dressing of ESTERICIDE® gel was applied over the puncture site. A second application of the present formulation was performed as described within one month post-treatment with radiographic and tomographic monitoring of the lesion.

EXAMPLE 6

Treatment Method for Regeneration of Cartilage for Arthropathy of Elbow Joint

The elbow remains slightly flexed and supported over a pillow with the wrist in a neutral position. With antisepsis, local anesthesia was cutaneously administrated. The skin entry site was in a depression zone located immediately proximal to radial head. After ensuring the correct puncture location, 2 mL of formulation 2 of the present invention is perfused. A protective dressing of ESTERICIDE® gel was applied over the puncture site. A second application of the formulation of the present invention was administered as described before, one month post-treatment, with radiographic and tomographic monitoring of the lesion.

EXAMPLE 7

Treatment Method for Regeneration of Cartilage for Arthropathy of Wrist Joint

The elbow remains slightly flexed while the wrist in rolled inward and in a neutral position. With antisepsis, local anesthesia is cutaneously administrated. The skin entry site is over the dorsal position of the wrist's articulation, just above the site with the highest sensitivity. After ensuring the correct puncture location, 2 mL of formulation 2 of the present invention is perfused. A protective dressing of ESTERICIDE® gel is applied over the puncture site. A second application of the formulation of the present inven-

EXAMPLE 8

Treatment Method for Regeneration of Cartilage for Arthropathy of Glenohumeral Joint The procedure must be performed with an anterior approach. The patient's hands are placed to rest over his/her lap remaining still without moving the arms or shoulders. With antisepsis, intramuscular infiltration of lidocaine (2%) is performed. The skin entry site is just below and medial to the posterolateral aspect of the acromion, and from this posterior approach, the needle tip is directed towards the coracoid process. After ensuring the correct puncture location, 2 mL of formulation 2 of the present invention was perfused. A protective dressing of ESTERICIDE® gel was applied over the puncture site. A second application of the present formulation was administered as described before, one month post-treatment, with radiographic and tomographic monitoring of the lesion.

EXAMPLE 9

Treatment Method for Regeneration of Cartilage for Arthropathy of Knee

With antisepsis, intramuscular infiltration of lidocaine (2%) was performed to the knee in a semiflexed position (45°). The medial border of the patellar tendon was located and a puncture with an hypodermic needle was performed, perpendicularly to skin, immediately medial to patella until reaching the articular and synovial capsule. Synovial fluid was extracted to assure the correct location of the puncture and 2 mL of formulation 2 of the present invention was perfused. A protective dressing of ESTERICIDE® gel was applied over the puncture site. A second application of the present formulation was administered as described above, one month post-treatment, with radiographic and tomographic monitoring of the lesion.

EXAMPLE 10

Treatment Method for Regeneration of Cartilage for Coxarthrosis

Sedation of the patient was performed as well as antisepsis of the surgical area. The puncture site is located in the coxofemoral joint region, the major vortex of trochanter was situated approximately 6 cm straightforward to imaginary middle line of body and 6 cm from there to a cephalic direction. With the use of fluoroscopy, the needle insertion site was located and a blocking needle is introduced to perfuse 2 mL of formulation 2 of the present invention. A protective dressing of ESTERICIDE® gel was applied over the puncture site. A second application of the present formulation was administered as described before, one month post-treatment, with radiographic and tomographic monitoring of the lesion.

EXAMPLE 11

Treatment of Long Bone (Femur) Fracture

Figure 1B:
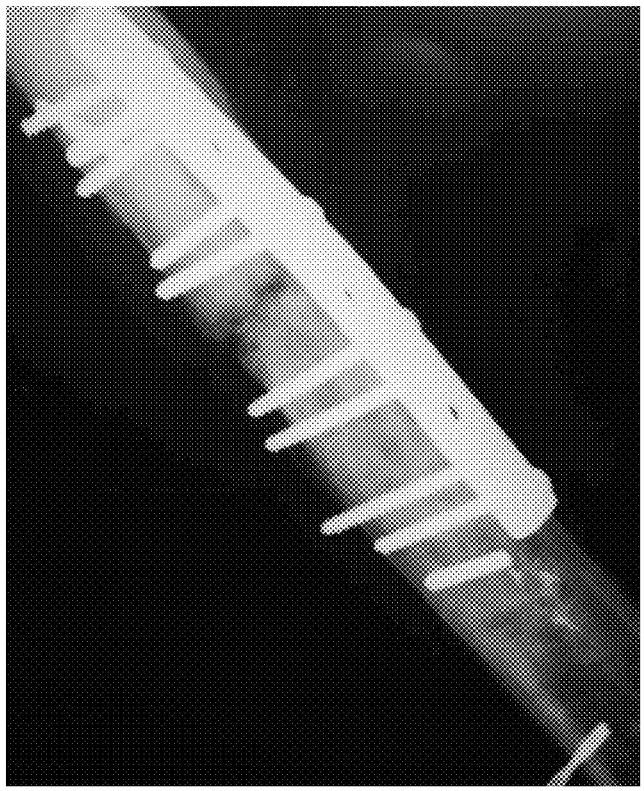

A 26 year old male patient with 12 previous surgeries presented with 13 year-old atrophic femoral pseudoarthrosis. His x-ray revealed a femur fracture supported by a fixation plate and ten screws (FIG. 1A). Under percutaneous local anesthesia and antisepsis with ESTERICIDE® antiseptic, 2 mL of the present formulation 2 were perfused intralesionally using a fluoroscope and peripheral nerve block catheter. Finally, a protective dressing of antiseptic ESTERICIDE® gel was placed on the puncture site. Twenty days post-treatment, a second application of the present formulation was administered. Forty days after the first treatment, radiographic imaging showed clear osteogenesis in the center of fracture (FIG. 1B).

EXAMPLE 12

Treatment of Double Facial (Parasymphysis and Mandibular Ramus) Fracture

Figure 2A:
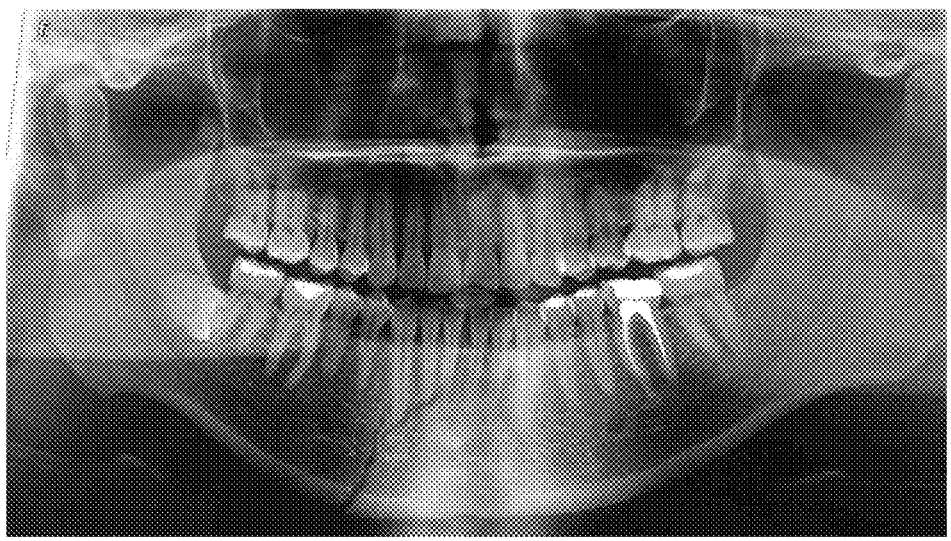
FIGS. 2A-2C are x-ray images of a patient with facial fractures.
Figure 2B:
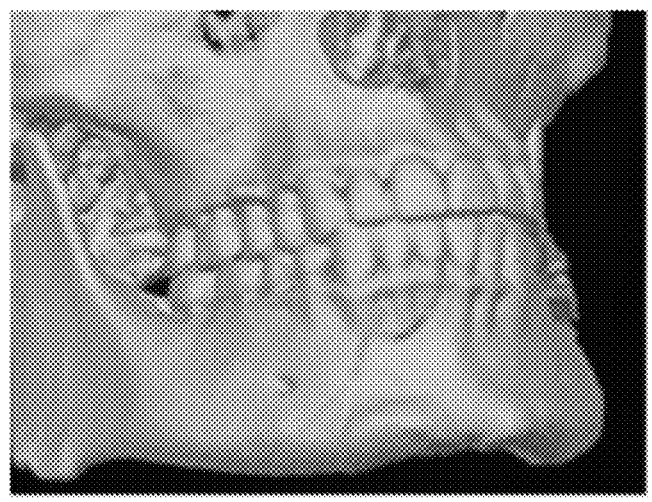
Figure 2C:
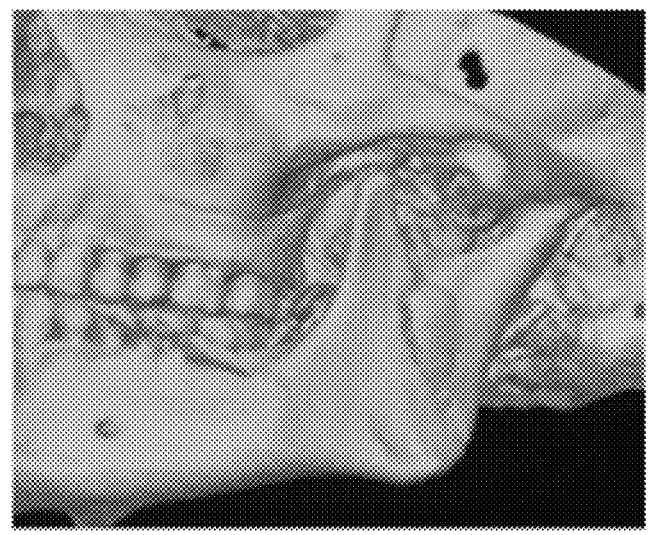

A 25 year old male patient presented with facial fractures. His x-ray revealed both a parasymphysis fracture and a fracture of the left mandibular ramus (FIG. 2A). Under general anesthesia and antisepsis with ESTERICIDE®, external fixators were placed and 4 mL of the present formulation 2 (2 mL in each fracture niche) were perfused intralesionally using a fluoroscope. Finally, a protective dressing of ESTERICIDE® gel was placed on the puncture site. Twenty days post-treatment, the external fixators were removed and radiographic imaging showed consolidation of both fractures (FIGS. 2B-2C).

EXAMPLE 13

Treatment of Tooth Extraction and Osteoporosis

A 61 year old female patient with osteoporosis, controlled hypertension and diabetes presented with an acute infection in the root fragments of the inferior first right molar tooth with submaxillary cellulitis (FIG. 3A). The patient insisted her tooth be removed but accepted treatment with the formulation of the present invention to repair the bone defect due to extraction and osteoporosis. After eradication of the infection, extraction of the tooth was performed under local anesthesia and the surgical bed was washed with antiseptic. Subsequently, an aspiration needle filled with 2 mL of formulation 2 was introduced to the surgical bed until cancellous bone was reached and the formulation was slowly perfused.

Osteogenesis was observed by radiographic imaging, ten days post-treatment (FIG. 3B). An important increment of bone density was observed not only in the extraction zone, but within the zone of osteoporosis damage so she was referred after one month for clinical and radiographic monitoring. Thus, it was demonstrated that the formulation of the present invention is a therapeutically effective treatment for osteoporosis disease.

EXAMPLE 14

Treatment of Osteomyelitis, Osteoporosis and Facial Fracture

A 60 year old female patient presented with osteoporosis, post-surgical osteomyelitis of 4 years and a fracture in the ascending ramus of the mandible. The patient also had a neoplasia in the current injured zone and osteomyelitis occurrence after its enucleation and curettage.

An antiseptic solution (ESTERICIDE®; 3 mL) was applied intralesionally, two times per week, for six weeks and oral antibiotics were also prescribed which eradicated the infection. An initial panoramic x-ray showed severe bone degradation (FIG. 4A). After eradication of osteomyelitis and under general anesthesia, 3 mL of the present formulation 2 were perfused intralesionally, using fluoroscopy. Then, an external fixator was placed for stabilization of the mandible. The external fixator is a substitute for the reconstruction plates that must be placed with the surgical procedure. Finally, a protective dressing of superoxide electrolyzed solution and gel was placed over the external wounds.

Fifteen days post-treatment, clinical and radiographic monitoring revealed an increase in bone density around the injury. One month post-treatment, (FIG. 4B) a panoramic image revealed the formation of new bone close to the right fixator apex (arrow) with no recurrence of osteomyelitis. A second application of the present formulation was made as described above. After one month, the patient was monitored clinically and radiographically which showed that the procedure eliminated 4 year old osteomyelitis and induced osteogenesis.

EXAMPLE 15

Figure 5A:
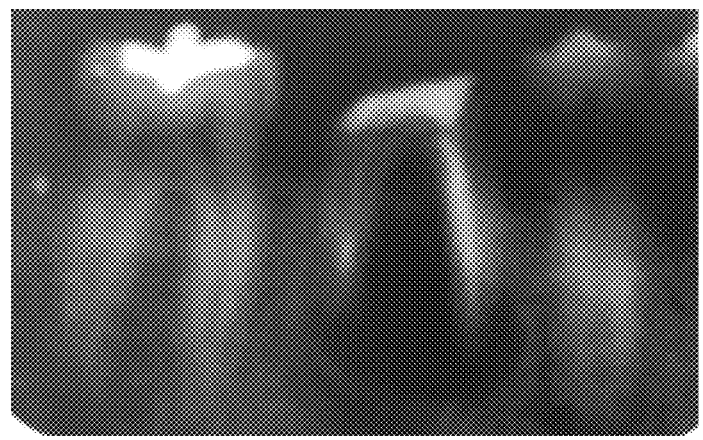
FIGS. 5A-5C are apical x-rays of a patient with a dentoalveolar fracture with periodontal tissue damage and an apical cyst.

Treatment of Dentoalveolar Fracture with Periodontium Damage and Apical Cyst with Bone Destruction A 28 year old male patient with a root canal of tooth 30, presented with a coronal horizontal fracture, major loss of the clinical crown and an apical cyst with bone destruction, loss of the periodontal ligament and rhizolysis (FIG. 5A). The dental organ was severely damaged and exodontia was necessary but the patient agreed to treatment with formulation 1 of the present invention.

Figure 5B:
Figure 5C:
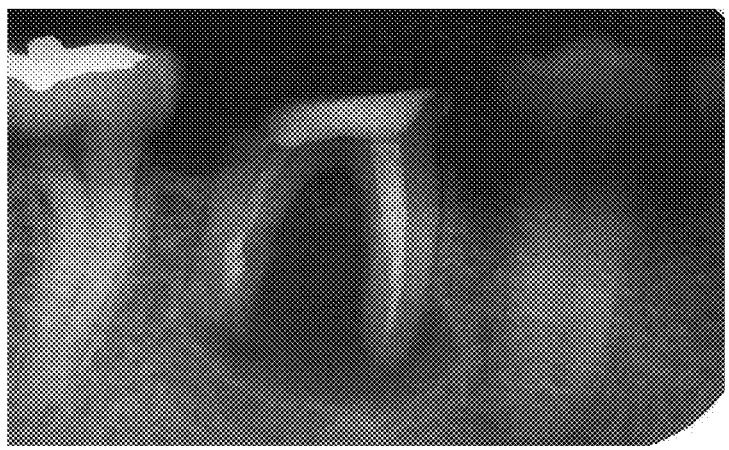

The treatment was performed under local mandibular nerve block anesthesia (Mevipacaine; 1 mL; 3%), antisepsis with ESTERICIDE®. Then, an aspiration needle was used to extract less than 0.5 mL of bloody exudate by negative aspiration and 2 mL of the present formulation were slowly perfused. Seven days post-treatment, radiography showed osteogenesis and regeneration of the horizontal coronal fracture (FIG. 5B). A second dosage of the present formulation was administrated and radiography fourteen days post-treatment showed bone regeneration, treatment of root resorption as well as regeneration of the periodontal ligament, treatment of the mesial root rhizolysis gaps (FIG. 5C).

EXAMPLE 16

Treatment of Dental Organs with Periodontal Disease and Root Resorption

Figure 6A:
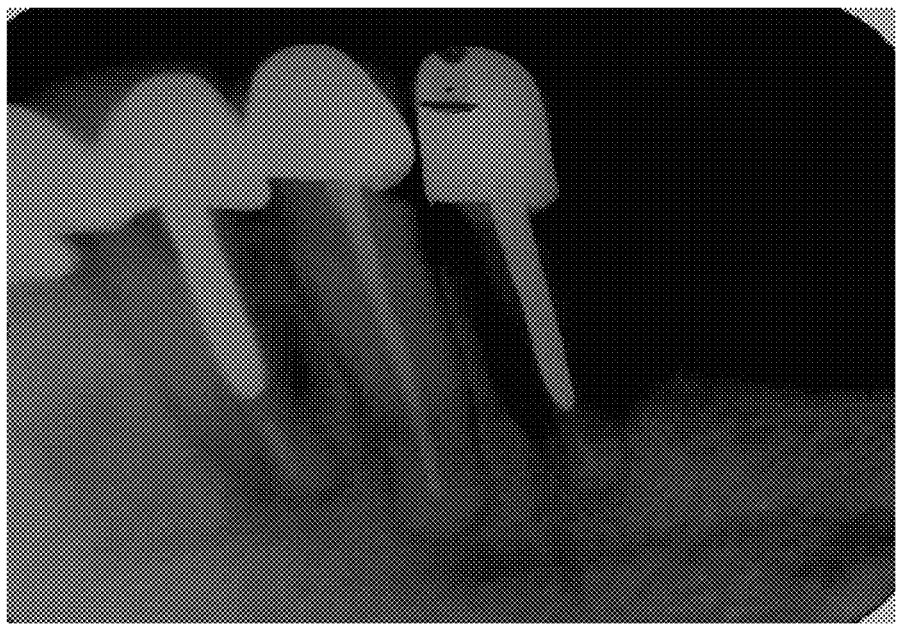
FIGS. 6A-6B are apical x-rays of dental organs with periodontal disease and root resorption.

A 78 year old male patient presented with periodontal disease in the anterior dental organs with superior and middle third root resorption of tooth 44 and tooth 42 (FIG. 6A). The dental organs were severely damaged and exodontia was mandatory. The patient agreed to treat his teeth with formulation 1 of the invention.

Figure 6B:
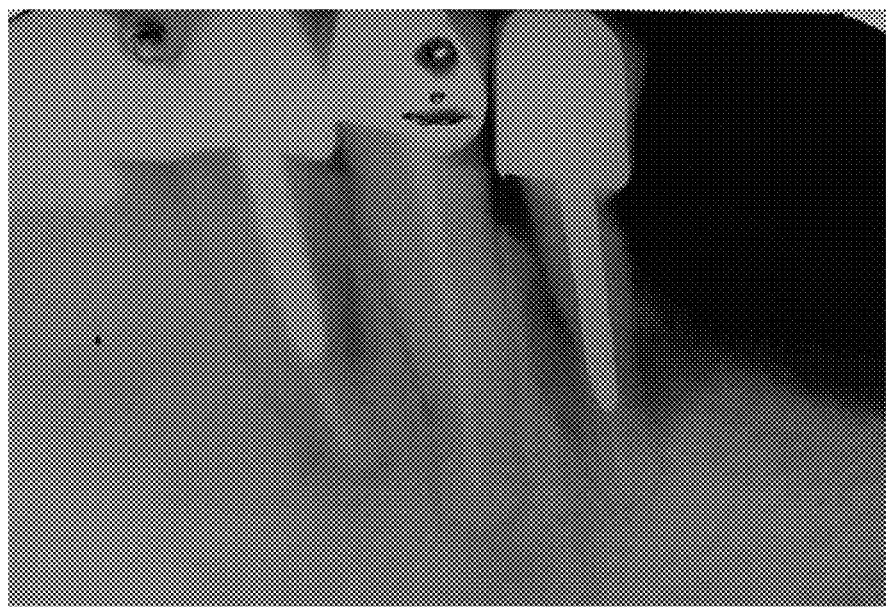

Under local mandibular nerve block anesthesia, scaling was performed along with antisepsis with ESTERICIDE®. Then, 2 mL of the formulation of the present invention were applied peri- and intraligamentarily. Fifteen days post-treatment, there was full regeneration of the damaged teeth and osteogenesis of the injured bone (FIG. 6B). Thus, the formulation of the present invention was able to regenerate the damaged bone and periodontal ligament and also dentin and cement.

EXAMPLE 17

Treatment of Left Knee Arthropathy with Cartilage Regeneration

An 84 year old female presented with Hallus Valgus left knee arthropathy of 10 years (FIG. 7A). After antisepsis of the knee surface, lidocaine (2%) was administered via intramuscular infiltration of the knee in a semiflexed position)(45°) Then, 2 mL of the present formulation were injected in the medial border of the patellar tendon perpendicular to the skin, immediately medial to the patella reaching the articular and synovial capsule. Formulation 2 of the present invention was slowly perfused and a protective dressing of ESTERICIDE® gel was applied over the puncture site. After 21 days, the patient showed remarkable improvement in walking and knee flexibility, as well as chondrogenesis (FIGS. 7B-7C). A second application of the formulation was administered a week later as described. After 4 months, the patient's mobility and flexibility was significantly improved.

EXAMPLE 18

Treatment of Coxarthritis with Cartilage Regeneration

Figure 8A:
FIGS. 8A-8B are x-rays of a patient with coxarthrosis and post-infection femoral bone shortening due to a fracture in the left hip.
Figure 8B:
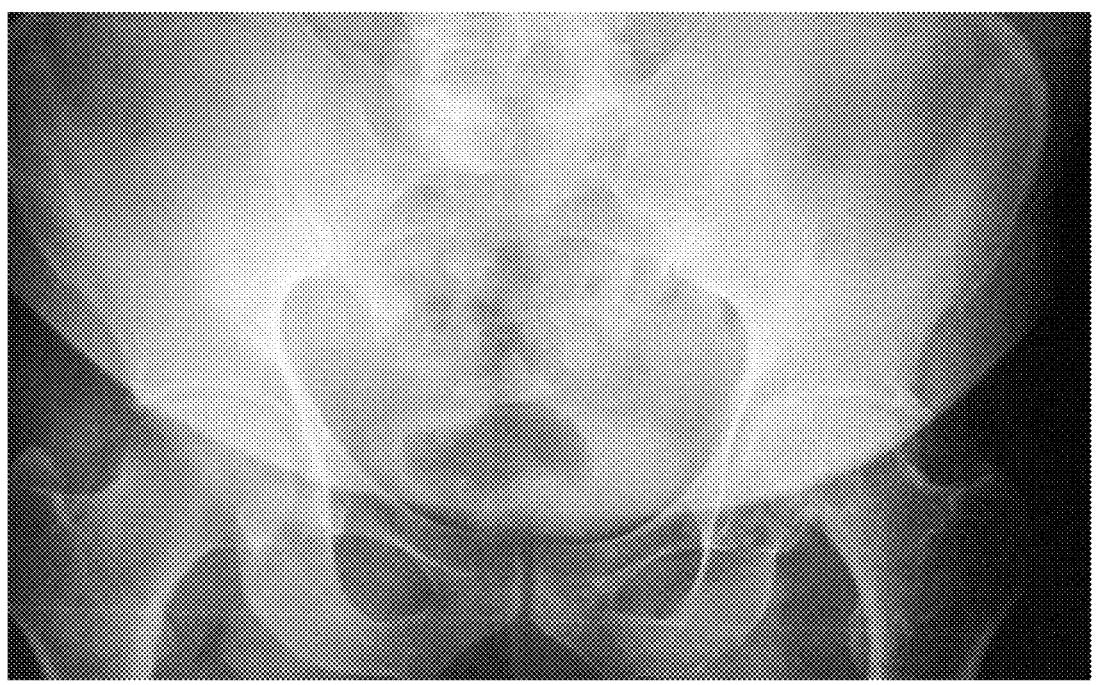

A male patient presented with coxarthrosis and post-infection femoral bone shortening due to a fracture in the left hip (FIG. 8A). The recommended treatment is arthroplasty and vigorous physical rehabilitation. The patient, however, agreed to treat his pathology with formulation 2 of the present invention. After sedation and antisepsis, 2 mL of the present formulation was administered into the coxofemoral joint region via fluoroscopy. The formulation was slowly perfused and a protective dressing of ESTERICIDE® gel was applied over the puncture site. One month post-treatment, there was a remarkable improvement of movement range and chondrogenesis at the site of the injury (FIG. 8B).

EXAMPLE 19

Treatment of Dentigerous Cyst

Figure 9A:
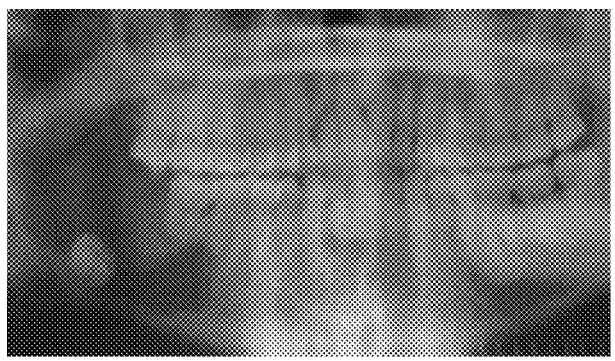
FIGS. 9A-9F are x-rays of a dentigerous cyst lesion in the lower right side of the mandible.
Figure 9B:
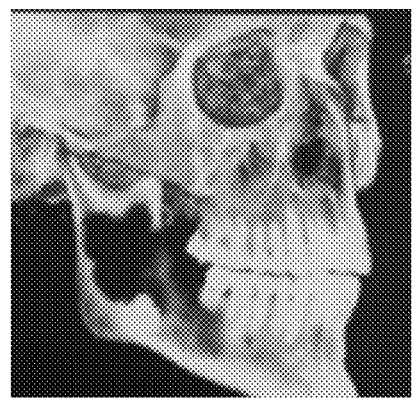

A 21 year old male patient presented with slight hyperaesthesia and a right mandibular osteolytic lesion. Radiolography showed a multilocular lesion with rhizolysis, a defined capsule and destruction of the external and internal cortical bone, encompassing the body and ascending ramus of the mandible. There was a developing dental organ in the ectopic position, near the mandibular basal bone with a clinical crown and rhizolysis in the apical third of the second lower right molar (FIGS. 9A-9B). Typical treatments include marsupialization, subsequent removal of the cystic capsule, enucleation and curettage of the neoplasia, which has a risk of recurrence. The patient agreed to treat his pathology with formulation 1 of the present invention.

Local anesthesia (Mepivacaine; 1 mL; 3%) was given subdermally in the right pre-auricular region after antisepsis with ESTERICIDE®. Subsequently, an aspiration needle was used to extract 9 mL of the intracystic liquid. Then, 2 ml of the formulation of the present invention was slowly perfused. A protective dressing of antiseptic electrolyzed solution and gel was placed over the puncture site.

Figure 9C:
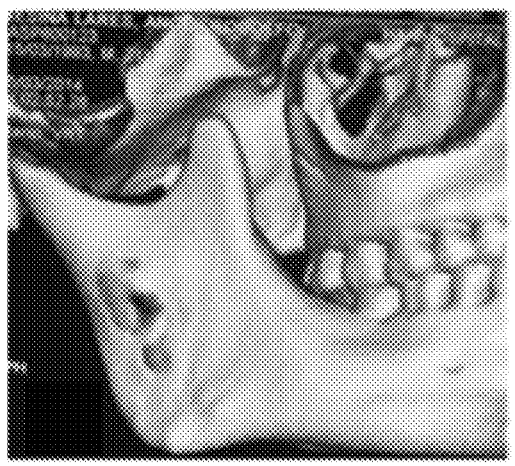
Figure 9D:
Figure 9E:
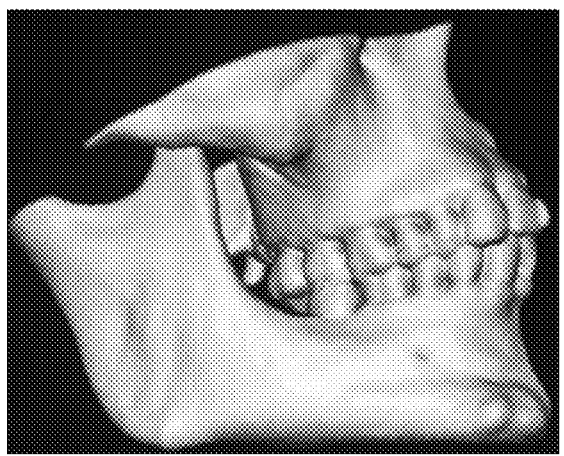
Figure 9F:
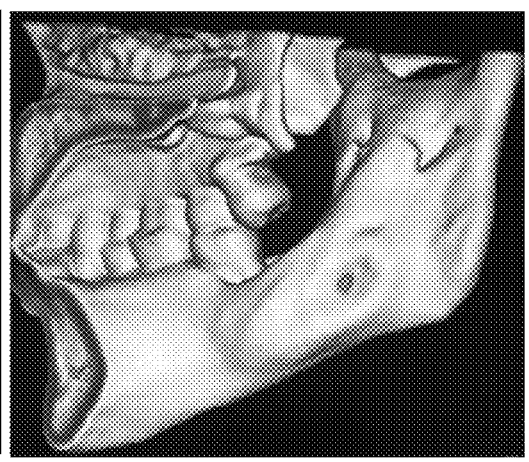

Seven days post-treatment, radiography revealed intra- and extra-lesional osteogenesis and resorption of the bone was observed after one month due to the presence of the non-erupted dental organ and the multilocular nature of the lesion. Therefore, a second application of the present formulation was performed two months after the first application. Tomography seven days later showed regeneration of the external cortical bone and the cancellous bone (FIGS. 9C-9D). Two months post-treatment, extraction of the non-erupted tooth along with its cystic capsule was performed and after five months, tomography showed regeneration and remodeling of the injury (FIGS. 9E-9F).

EXAMPLE 20

Treatment of Bilateral Mandibular Fracture, Odontogenic Tumors and Cyst

A 19 year old female with perinatal cerebral hypoxia and Gorlin Goltz syndrome presented with a bilateral mandibular fracture, two keratocystic odontogenic tumors, three odontomas (compound, complex and cystic) and a dentigerous cyst (FIG. 10A). Placement of reconstruction plate and ulterior iliac bone graft along with curettage or enucleation of remaining cystic lesions was highly recommended. Informed consent (Helsinki's protocol) for formulation 1 of the present invention was obtained.

Under general anesthesia, after antisepsis with ESTERICIDE®, an aspiration needle with a 20 mL syringe was introduced intralesionally in the right keratocystic tumor, 4 mL of seropurulent exudate was extracted with negative pressure and the lesion was washed with an antiseptic solution. Finally, 2 mL of the present formulation were perfused into the lesion. Next, an aspiration needle with a 10 mL syringe was introduced intralesionally in the dentigerous cyst, 2 mL of a dense yellowish fluid was extracted by suction, and 1 mL of formulation 1 was slowly perfused into the cyst.

For treatment of the odontomas, 1 mL of serohematic fluid was extracted from each mandibular odontoma and 0.5 mL of the present formulation was slowly perfused into each odontoma. The complex odontoma, located on the left side of the maxilla, was treated with 1 mL of the present formulation after extraction of 0.5 mL of serohematic fluid.

Finally, a protective dressing of an antiseptic electrolyzed solution and gel was applied over the puncture site. Five days post-treatment, radiography revealed full consolidation of the fractures and clear evidence of a decrease of the cystic lesions (FIGS. 10B-10D). The fixator was removed and enucleation of the right side of the keratocystic capsule was performed. Finally, 1 mL of the present formulation was perfused into the lesion and a protective dressing of superoxide gel was applied. The patient was monitored five months post-treatment (FIGS. 10E-10F) and had osteogenesis in the right side of the mandible and treatment of fractures, dentigerous cyst, keratocystic odontogenic tumor and odontomas.

EXAMPLE 21

Treatment of Keratocystic Odontogenic Tumor with Calcifying Areas

Figure 11A:
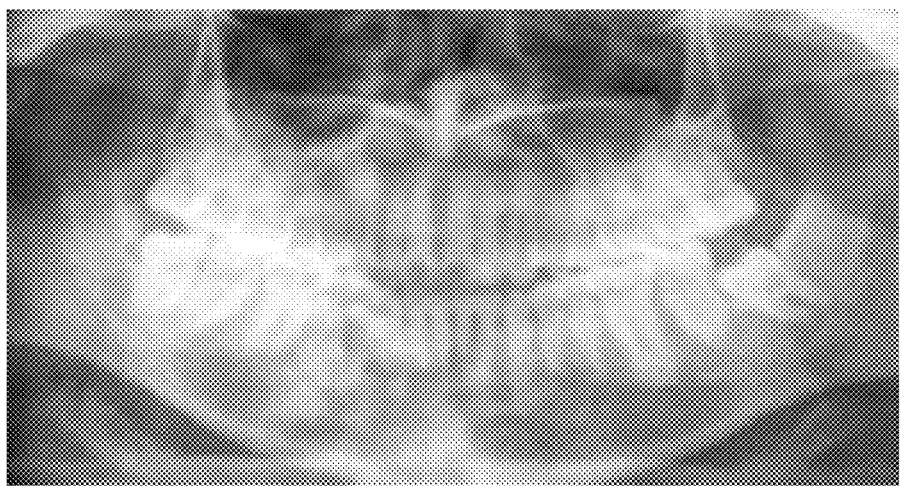
FIGS. 11A-11D are panoramic radiographies of an odontogenic keratocystic tumor and bilateral symphyseal region with multiple calcified areas.

A 22 year old male presented with pain in the right retromolar space and pericoronitis at the third molar. Laboratory tests were normal but panoramic radiography showed diffuse mandibular images with radiolucent and radiopaque regions in the body and the symphyseal area (FIG. 11A). Histopathological examination revealed a keratocystic odontogenic tumor congruent with nevoid basal cell carcinoma (Gorlin) syndrome. The patient agreed to treatment with formulation 1 of the present invention.

After antisepsis with ESTERICIDE®, local mandibular nerve block anesthesia (1.8 mL of DENTOCAINE®: Mepivacaine 36 mg, epinephrine 18 mg) was applied. The lesion was punctured with an aspiration needle between the inferior second premolar and first molar region. The extraoral approach was made under the bottom of the vestibular sac, avoiding any contact with the oral cavity and making rotational movements with the needle until penetration of the vestibular compact bone. After the biopsy, the present formulation was introduced intralesionally and slowly perfused. Finally, a protective dressing of an antiseptic electrolyzed solution and gel was placed over the puncture.

Figure 11B:
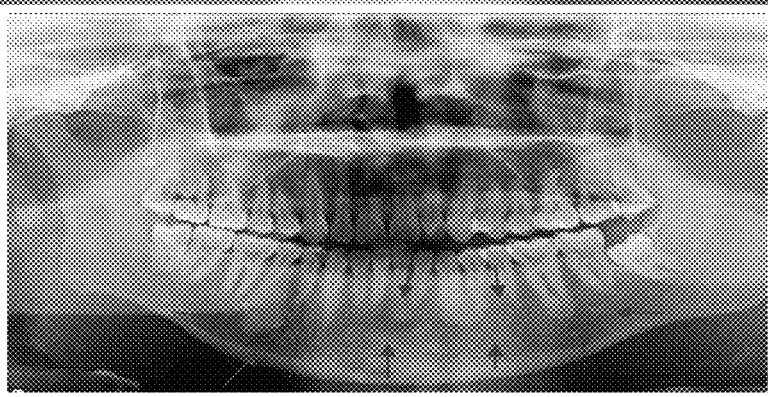
Figure 11C:
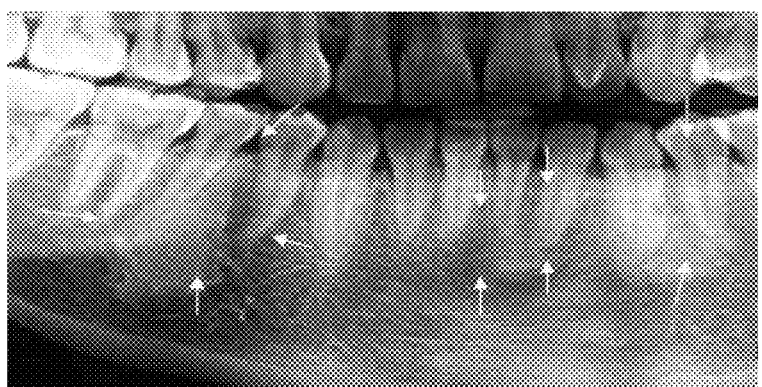
Figure 11D:
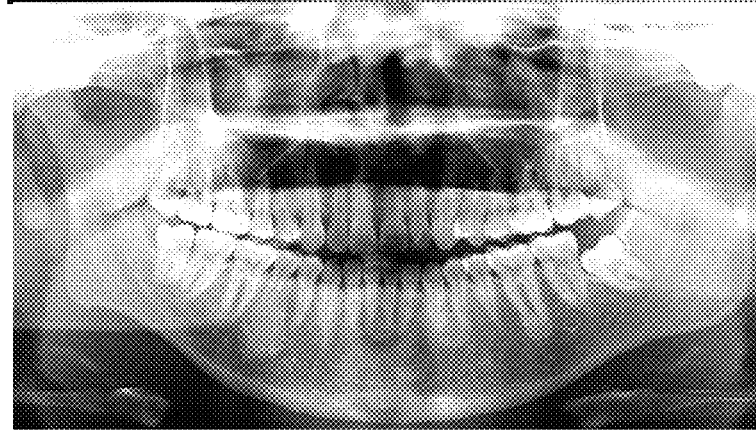

Tomography seven days post-treatment (FIGS. 11B-11C) showed regeneration of mandibular trabecula without the appearance of hypercalcified areas and an increase in bone density. Three months post-treatment, tomography (FIG. 11D) showed osteogenesis of healthy cancellous bone at the injury.

EXAMPLE 22

Treatment of Borderline Ameloblastoma with Calcifying Cyst Odontogenic Tumor (CCOT)

Figure 12A:
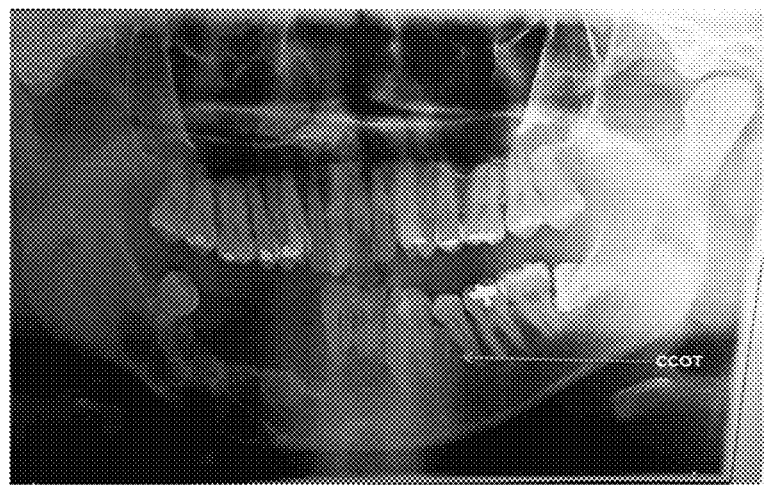
FIGS. 12A-12G are x-rays of a borderline unicystic plexiform ameloblastoma in the right hemimandible and a calcifying cyst odontogenic tumor (COOT).

A 26 year old patient presented with paresthesia, a borderline unicystic plexiform ameloblastoma of the mandible and a calcifying cyst odontogenic tumor in the right hemimandible (FIG. 12A). The patient agreed to treatment with formulation 1 of the present invention.

Treatment was made under bilateral nerve block anesthesia with Mepivacaine 3%, after antisepsis with ESTERICIDE®. A needle with syringe was inserted intralesionally, via a mental and submental percutaneous approach, for the aspiration of 37 mL of serohematic exudate. With the same procedure, 4 mL of the present formulation were injected: 2 mL in the back side of tumor and 2 mL in the mental area of the tumor perfusing into all of the intralesional locules so as to reach the perimeter of the lesion.

Figure 12B:
Figure 12C:
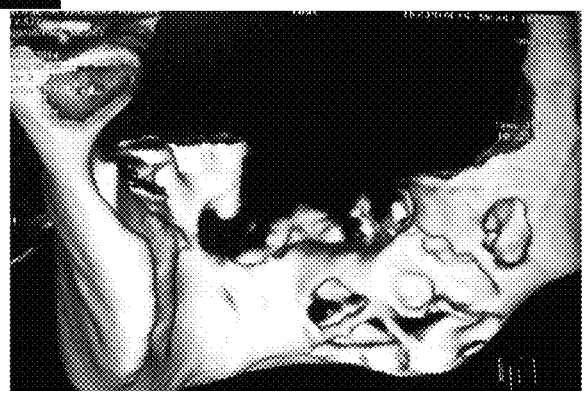
Figure 12D:
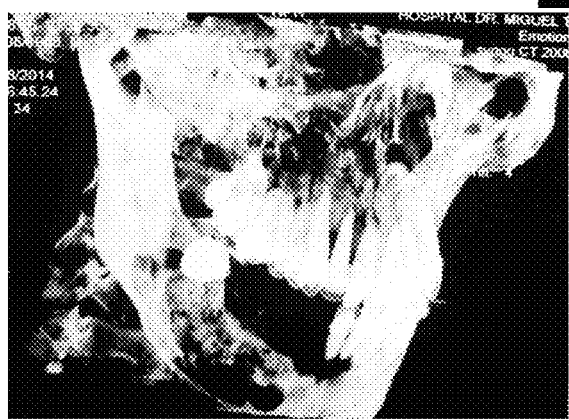
Figure 12E:
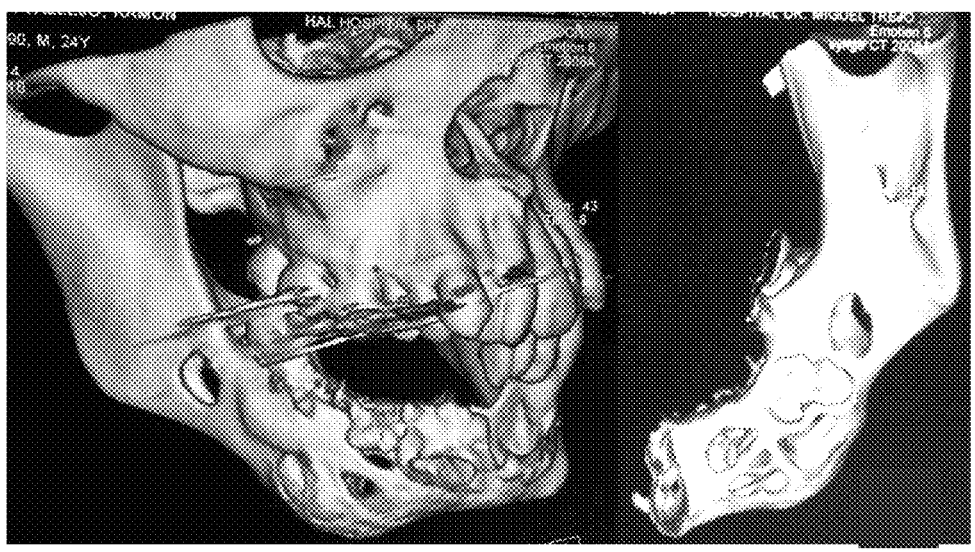
Figure 12F:
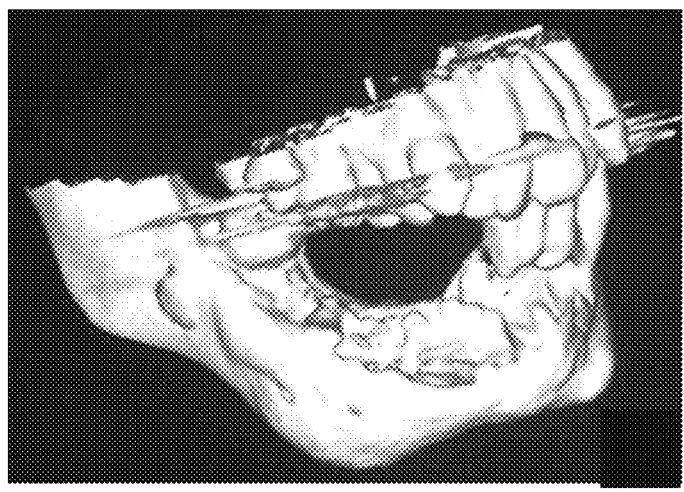
Figure 12G:
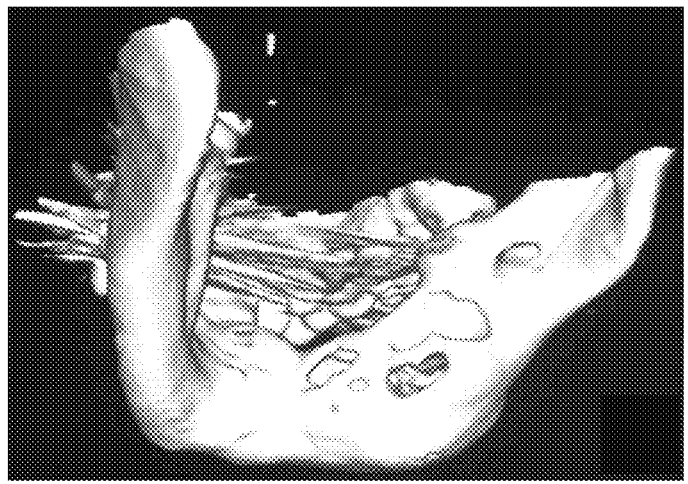

Three days later, 20 mL of intralesional exudate were extracted as described above. Seven days post-treatment, tomography (FIGS. 12B-12C) showed remarkable bone regeneration, including bony bridges and external cortical bone. Three days later, 3 mL of intralesional exudate were extracted and a second application of the present formulation was performed as described above. Radiography five days later showed no metastasis but little resorption of the neoformed bone and no further osteogenesis was observed. In contrast, a tumor capsule within dentoid structures and bone spicules was observed to be extended over the lesion (FIG. 12D). The capsule was removed after one month and a third intralesional application of the present formulation (2 mL) was made. One month later, tomographies showed osteogenesis at the lesion (FIG. 12E). Three months after the third application of the present formulation, a remarkable osteogenesis (95%) was observed (FIGS. 12F-12G).

EXAMPLE 23

Treatment of Gorlin's Tumor

Figure 13A:
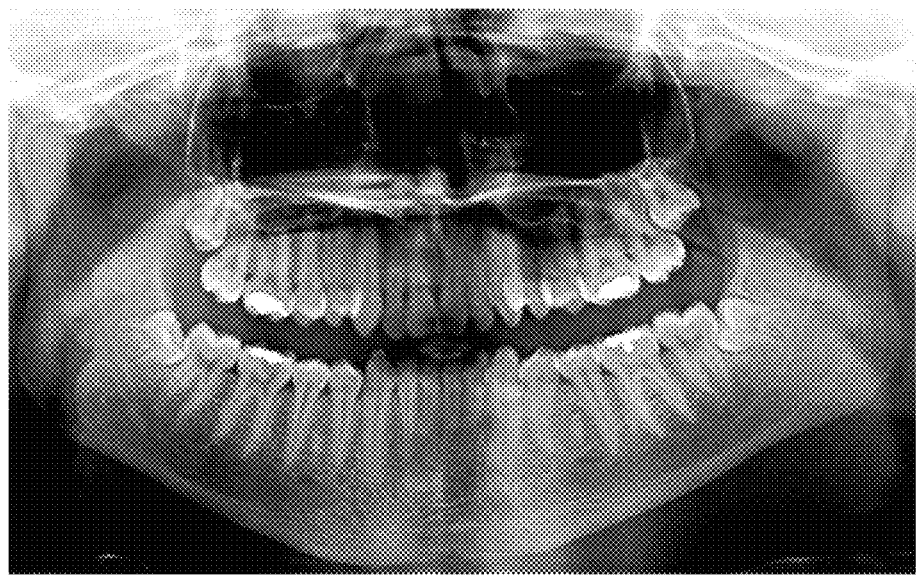
FIGS. 13A-13B are x-rays of a Gorlin's tumor in the left inferior premolar region.

A 17 year old male presented with a cystic lesion comprised of a dentoid-like calcification within a well formed cystic capsule, located in the apical and half region of the left inferior premolars, congruent with a Gorlin's tumor (FIG. 13A). Treatment includes enucleation of the cystic capsule but the patient agreed to treatment with formulation 1 of the present invention.

Figure 13B:

After antisepsis with ESTERICIDE®, local mandibular nerve block anesthesia (Mepivacaine; 1 mL; 3%) was administered. Then, 1 mL of the formulation of the present invention was intralesionally slowly perfused. Finally a protector deposit of an antiseptic electrolyzed solution and gel was placed over the puncture site. Seven days post-treatment, a periapical radiography showed complete bone regeneration of the injured zone with absence of a peripheral cystic contour (resorption of capsule) along with normal trabecular bone formation (FIG. 13B).

EXAMPLE 24

Treatment of Keratocystic Odontogenic Tumor

Figure 14A:
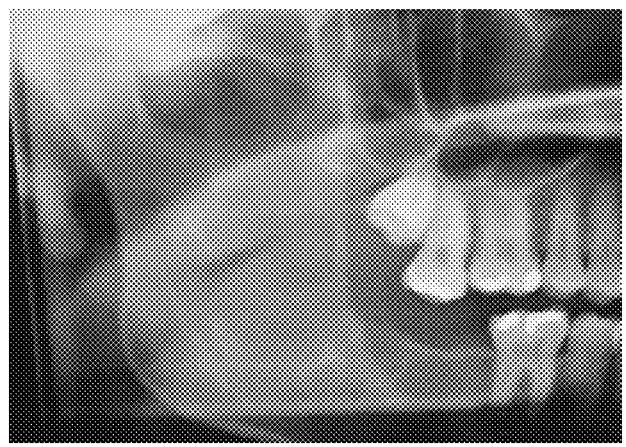
FIGS. 14A-14G show tomography of a multilocular keratocystic odontogenic tumor in the right side of the mandible.
Figure 14B:
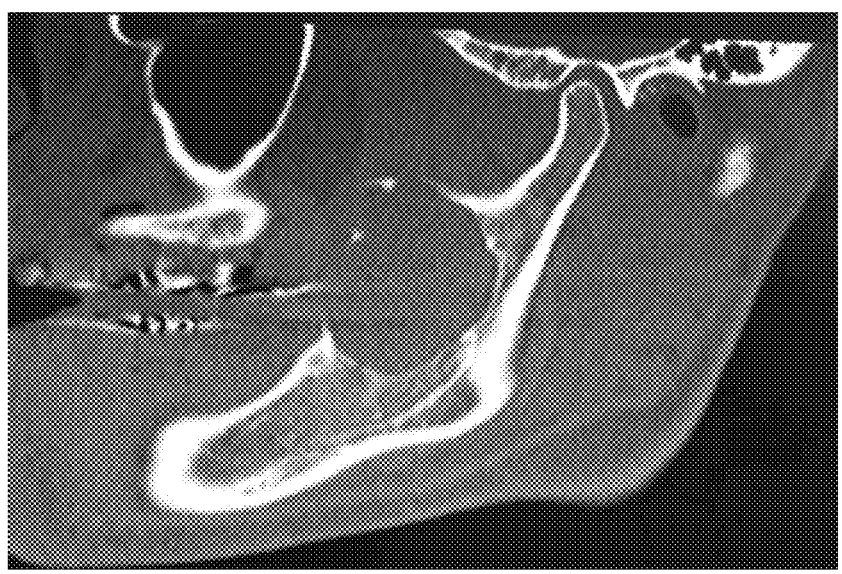

A 20 year old male presented with a mandibular cyst. Radiography showed a lytic mandibular multilocular lesion on the right side with intralesional liquid, comprising the ascending ramus, body, condyle, coronoid apophysis and premolars (FIGS. 14A-14B). A keratocystic odontogenic tumor after biopsy, and the patient agreed to treatment with formulation 1 of the present invention.

Figure 14C:
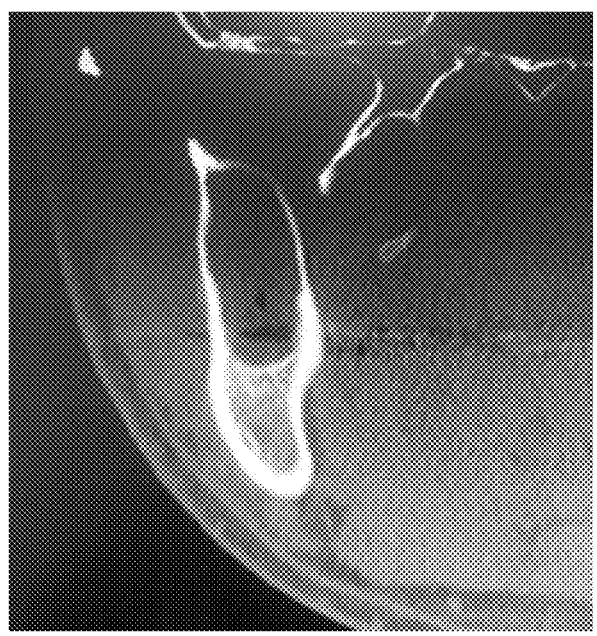
Figure 14D:
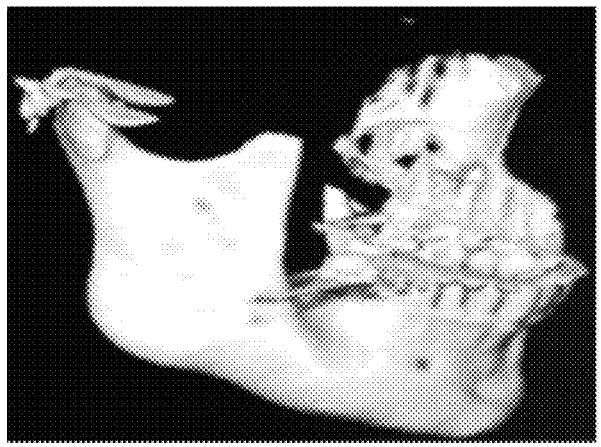
Figure 14E:

The patient had mandibular nerve block anesthesia (Mepivacaine; 1 mL; 3%) and antisepsis with ESTERICIDE®. Subsequently, an aspiration needle was used to extract by negative aspiration 25 mL of brown waxy intracystic content. Then, 2 mL of the formulation of the present invention was slowly perfused intralesionally. Finally, a protective dressing of electrolyzed gel was placed over the puncture site closed by a stitch. Three days post-treatment, tomography showed full regeneration of cortical and cancellous bone (FIGS. 14C-14E).

Figure 14F:
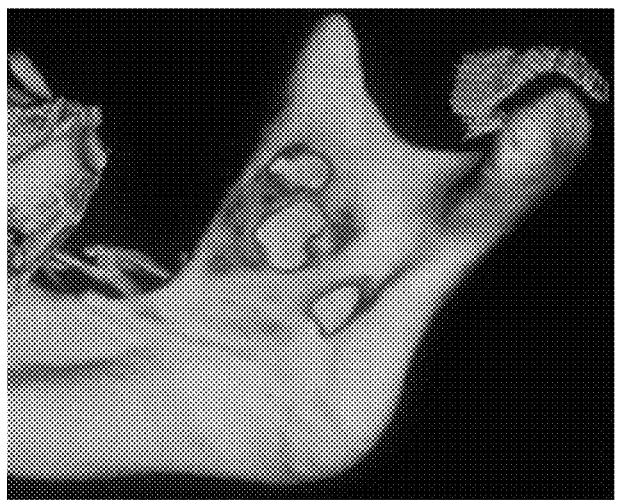
Figure 14G:

Eighty days post-treatment, the inner face of the condile showed partial regeneration, so 8 mL of a dark brown exudate were extracted and a second application of the present formulation was performed. Seven days post-treatment, tomography showed complete eradication of the cystic lesion and osteogenesis with regeneration of the injured tissues (FIGS. 14F-14G).

EXAMPLE 25

Treatment of Recurrent Aneurysmal Bone Cyst

A 13 year old male presented with a recurrent aneurysmal bone cyst of the mandible. The patient had two prior surgeries so an osteotomy was performed to cover the previous bone defect. Initial tomography showed a lytic lesion of the condyloid process of the mandible and a multilocular cystic region (with no well defined margins) of osseal hypodensity in the right ascending ramus (FIG. 15A). His second multiplanar tomography with reconstruction (FIG. 15B) showed a titanium miniplate (2.0 mm) with screws to hold the cortical osteotomy and a multilocular recurrent lesion. Typical treatment includes block resection of the right ascending ramus and further reconstruction with revascularized autologous bone from the iliac crest. The patient's parents agreed to treatment with formulation 1 of the present invention.

Due to the patient's age, the procedure was done under general anesthesia after antisepsis with ESTERICIDE®. An aspiration needle was inserted percutaneously and intralesionally into the temporal fossa for aspiration of 10 mL of hematic exudate. Next, 2 mL of formulation 1 of the present invention was injected via intralesional puncture. Finally, a protective dressing of an antiseptic electrolyzed solution and gel was placed over the puncture spots. Six days post-treatment, the patient's radiographic monitoring showed that the external cortical bone of the cystic lesion had completely healed and the presence of bone growth (FIGS. 15C-15D).

EXAMPLE 26

Treatment of Mandibular Ossifying Fibroma

Figure 16A:
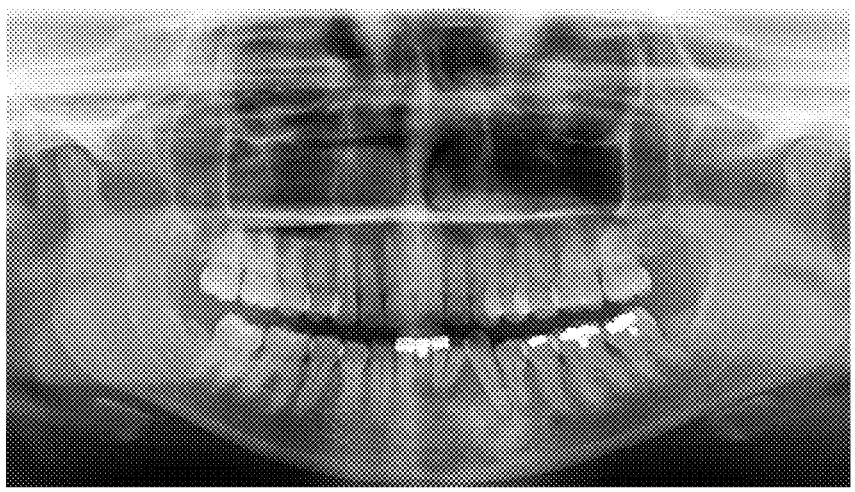
FIGS. 16A-16F are tomographies of a central mandibular ossifying fibroma of eight months.
Figure 16B:
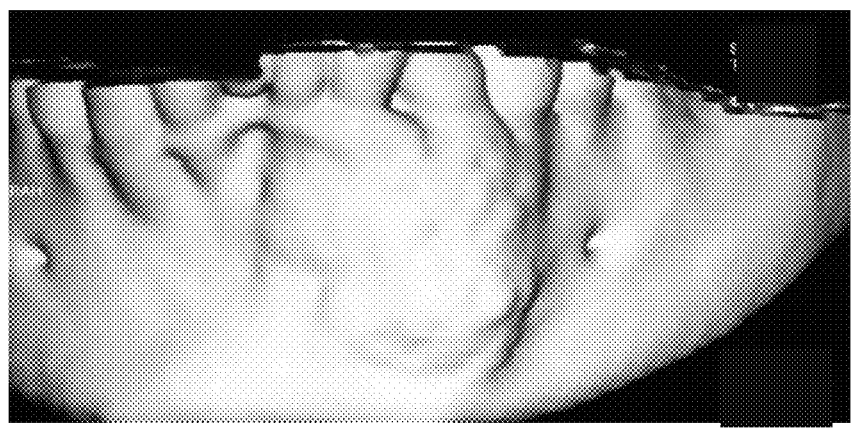
Figure 16C:
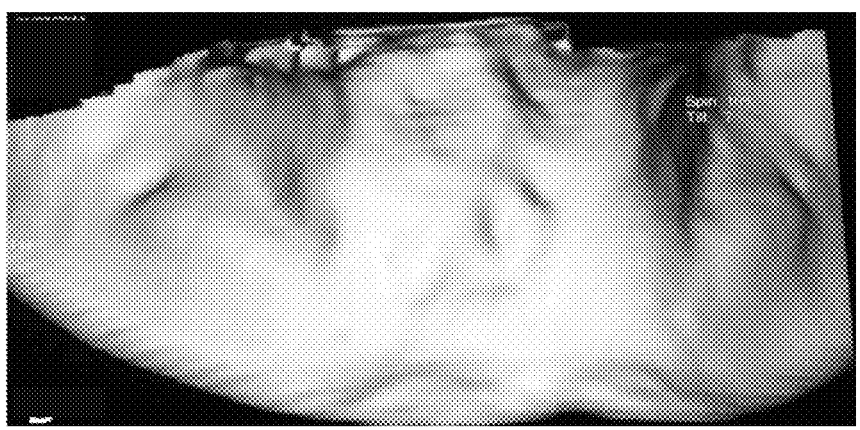

A 35 year old female presented with paresthesia due to a central mandibular ossifying fibroma of eight months. The lesion was an augmentation of the cortical bone without damage to the oral mucosa. Radiography revealed dental migration and characteristic bulkiness of the external bone tables, hyperdense bone areas with calcifying nodules and hypodense regions with loculi apparently filled with liquid (FIGS. 16A-16C). Recommended treatment is a block resection surgery but the patient agreed to treatment with formulation 1 of the present invention.

Figure 16D:
Figure 16E:
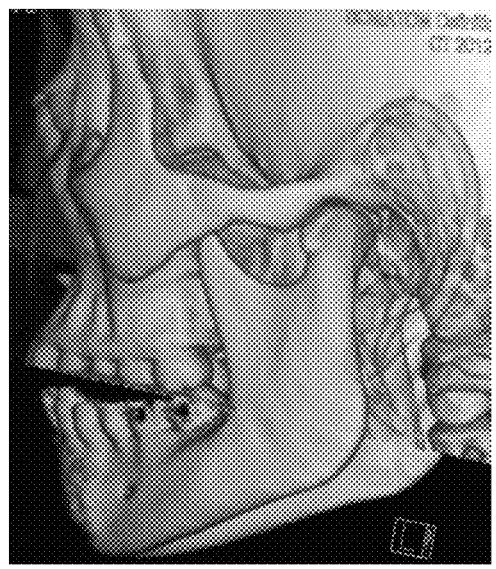
Figure 16F:
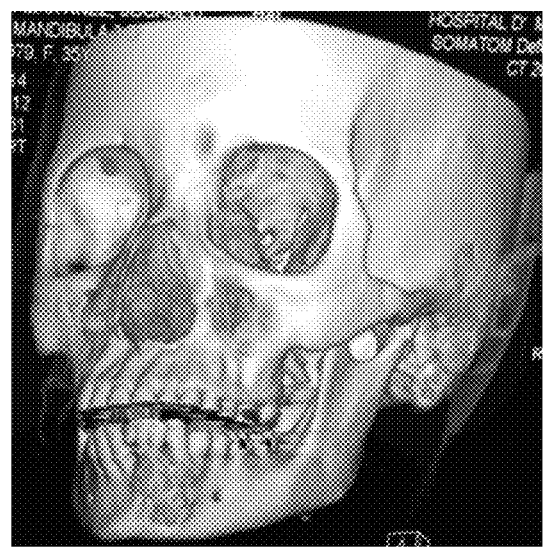

After antisepsis with ESTERICIDE®, local bilateral mandibular nerve block anesthesia (Mepivacaine; 1 mL; 3%) was administered. Subsequently, an aspiration needle was used to extract 2 mL of serohematic liquid by negative aspiration. Then, 3 mL of the formulation of the present invention was slowly perfused intralesionally. Finally, a protective dressing of antiseptic electrolyzed solution and gel was placed over the puncture site. Three days post-treatment a second application of formulation 1 was performed. Six days post-treatment, the paresthesia disappeared and tomography showed osteogenesis in the loculi (FIGS. 16D). Thirty-five days post-treatment, tomography showed diminishment of the lesion's bulkiness (FIGS. 16E-16F).

EXAMPLE 27

Treatment of Globulomaxillary Cyst

A 25 year old female presented with a globulomaxillary cyst and a low density lesion in the left side of the premaxilla (FIG. 17A). Conventional treatment for this kind of lesion is surgical enucleation which has a risk of recurrence. After obtaining informed consent (Helsinki's protocol), formulation 1 of the present invention was administered.

After antisepsis with ESTERICIDE®, infraorbital nerve block (1.8 mL of DENTOCAINE®: Mepivacaine 36 mg, epinephrine 18 mg) and palatal-anterior anesthesia (1.8 mL of DENTOCAINE® simple) was administered. Subsequently, the lesion was percutaneously punctured across the upper lip and 6 mL of yellowish brown liquid were extracted by negative aspiration. Then, 2 mL of the formulation of the present invention was slowly perfused intralesionally. A protective dressing of ESTERICIDE® gel was applied to the puncture sites. Seven days post-treatment, the patient's tomography showed initial osteogenesis within the cystic lesion. Radiography 14 days post-treatment revealed disappearance of the lesion and improved bone growth over the cystic lesion (FIG. 17B). 65 days post-treatment, there was complete osteogenesis within the original cystic lesion (FIGS. 17C-17D).

EXAMPLE 28

Treatment of Peripheral Dentigerous Cyst in Tooth 13

Figure 18A:
FIGS. 18A-18B are x-rays of a peripheral dentigerous cyst in tooth 13.
Figure 18B:
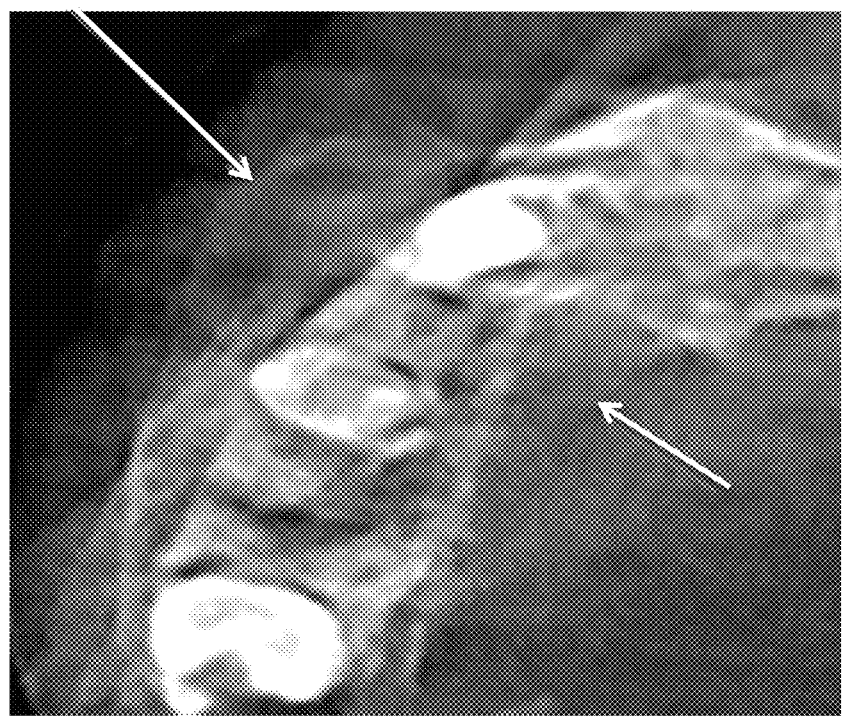

A 9 year old male presented with a peripheral dentigerous cyst in tooth 13 and radiography showed a cystic lesion (FIG. 18A) and was treated with formulation 1 of the present invention. Under sedation and local anesthesia and antisepsis with ESTERICIDE®, an aspiration needle was inserted intralesionally and 3 mL of a dense yellowish liquid were extracted by negative aspiration. Then, 2 mL of the formulation of the present invention were slowly perfused intralesionally. Finally, a protective dressing of ESTERICIDE® gel was applied at the puncture site. One month post-treatment, radiography showed osteogenesis within the original cystic lesion (FIG. 18B).

EXAMPLE 29

Figure 19A:
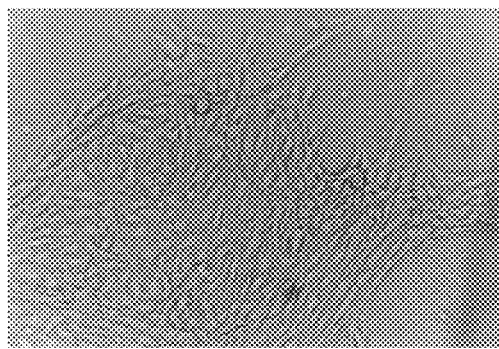
FIGS. 19A-19E show images of cell cultures.
Figure 19B:
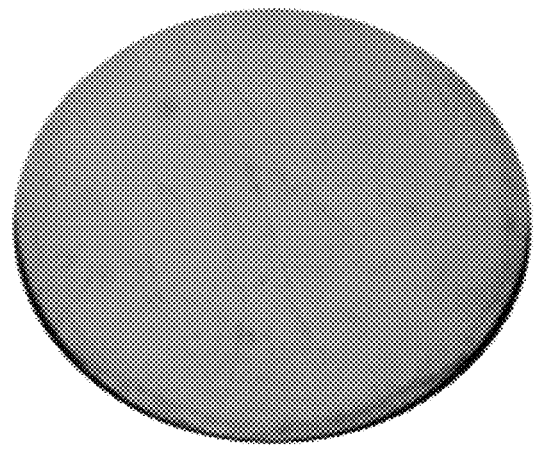

Detection of Stem Cells in the Intralesional Fluid of Treated Borderline Ameloblastoma and Comparison with Stem Cell Cultures Obtained from Dental Pulp Stem cells were obtained from dental pulp under conventional methodologies and cultured in petri dishes (35 mm×10 mm) in DMEM culture medium (FIG. 19A). Stem cells from the ameloblastoma were purified by filtration and centrifugation of the intralesional fluid and cultured under the above conditions. The obtained cells showed typical stem cells morphology (FIG. 19B).

Figure 19C:
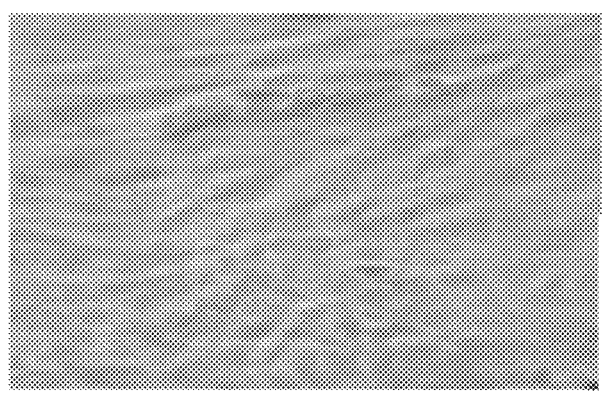
Figure 19D:
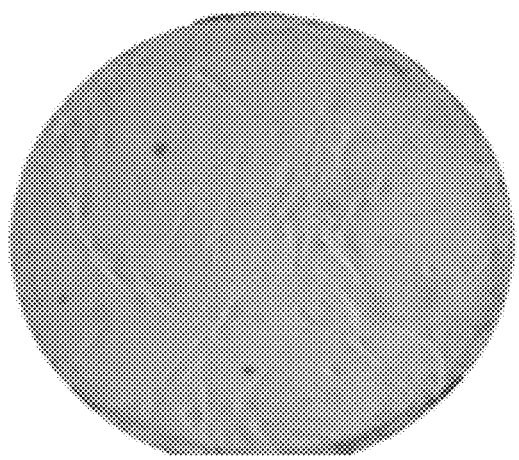
Figure 19E:
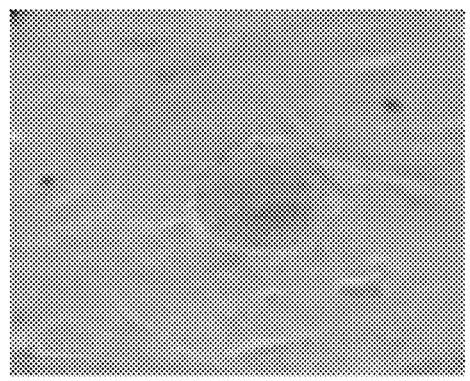

An equal number of the purified stem cells (1 mL) was cultured, as previously described, in three separated petri dishes and 1 mL of DMEM medium was added. Then, 5 µL/mL of formulation 1 of the present invention were added to the first dish, 5 µL/mL of formulation 2 of the present invention were added to the second dish and the third dish received no treatment. After two weeks, there was significant proliferation of the cells in dish one (FIG. 19C), apparent differentiation of cells in dish two into chondrocytes (FIG. 19D), and a modest quantity of cells with the typical fibroblastoid morphology in the control dish (FIG. 19E). Thus, this experiment demonstrated that the formulations of the present invention induce significant proliferation of cells in a short period of time and induce a change in the cellular lineage.

EXAMPLE 30

Treatment for the Stimulation of Hair Growth

Figure 20A:
FIGS. 20A-20B show a 72 year old male with partial alopecia in occito-parietal area before treatment with Formulation 1 (FIG. 20A) and ten days post-treatment (FIG. 20B).
Figure 20B:

A 72 year old male presented partial alopecia in occito-parietal area (FIG. 20A). The patient agreed to treatment with formulation 1 of the present invention. Under local anesthesia and antisepsis with ESTERICIDE®, an aspiration needle was inserted intradermically into different areas of the scalp and 1.5 mL of Formulation 1 were perfused from inside to outside, in order to stimulate both cellular niches and covering 15% of the alopecia area. Finally a protective dressing of ESTERICIDE® gel was applied at the puncture sites. Ten days post-treatment, the growth of hair was observed (FIG. 20B). A second application of the present formulation was administered 20 days post-treatment. Thus, the formulation of the present invention stimulates growth of hair and treat hair loss. In addition, as illustrated in FIG. 20B, the color of the patient's hair darkened after treatment with the formulation of the present invention and thus, this formulation may be used to stimulate pigmentation of the hair follicle.

Figure 21A:
FIGS. 21A-21C show a 62 year old male with hormonal alopecia before treatment with formulation 2 (FIG. 21A), 35 days post-treatment (FIG. 21B) and 65 days post-treatment with a second treatment administered at 30 days post first treatment (FIG. 21C).
Figure 21B:
Figure 21C:
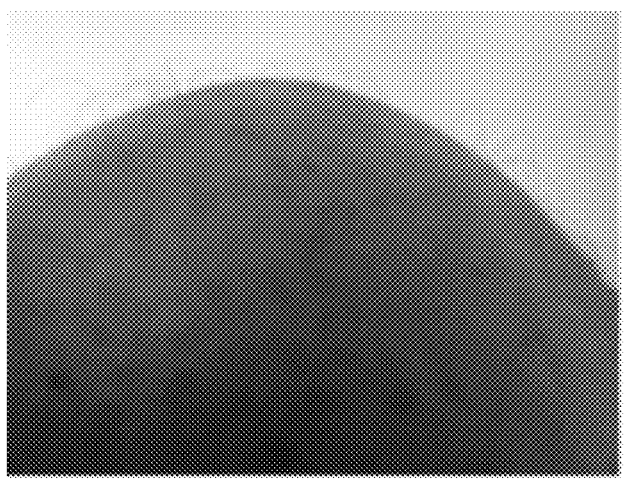

A 62 year old male controlled diabetic patient presented with a fifteen year-old hormonal alopecia (FIG. 21A). He agreed to treatment with formulation 2 of the present invention. After antisepsis with ESTERICIDE® an aspiration needle was inserted intradermically into different areas of the scalp and 1.5 mL of formulation 2 were perfused from inside to outside, in order to stimulate both cellular niches and covering the alopecia area by applying the formulation 2, each 2-5 cm. Finally a protective dressing of ESTERICIDE® gel was applied at the puncture sites. Formulation was applied weekly. 35 days post-treatment, the growth of hair was clearly observed (FIG. 21 B). A second treatment, as described before, was administered 30 days post-treatment in remanent areas of alopecia (FIG. 21C). A third treatment may be applied one or two months later, depending on observed results.

"Stimulating hair growth" includes stimulating an increase in total hair mass and/or length. Such increase includes increased length and/or growth rate of hair shafts (i.e. follicles), increased number of hairs, and/or increased hair thickness. "Stimulating hair growth" should also be considered to include preventing, arresting, decreasing, delaying and/or reversing hair loss such as might occur in, but not limited to, partial alopecia or hormonal alopecia. As is readily apparent, the present invention is further directed to a method for stimulating growth of hair and/or reducing hair loss in a subject in need of such treatment, comprising the step of contacting scalp with a formulation comprising a corticosteroid and at least one organic acid or a corticosteroid and an insulin analog.

EXAMPLE 31

Treatment of Septal Fistula Resultant from a Defective Rhinoseptoplasty

Figure 22A:
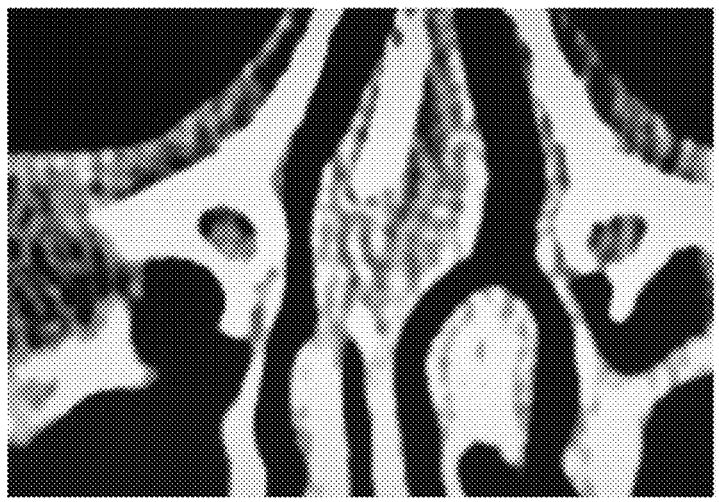
FIGS. 22A-22E are tomographies of a septal fistula over fifteen days post treatment.
Figure 22B:
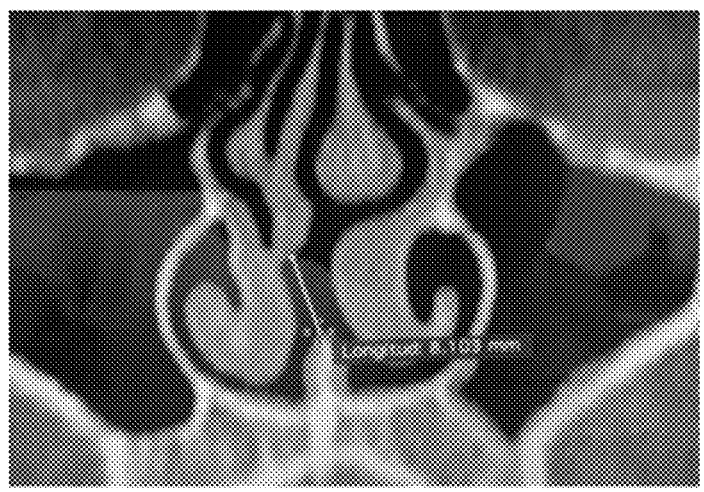
Figure 22C:
Figure 22D:
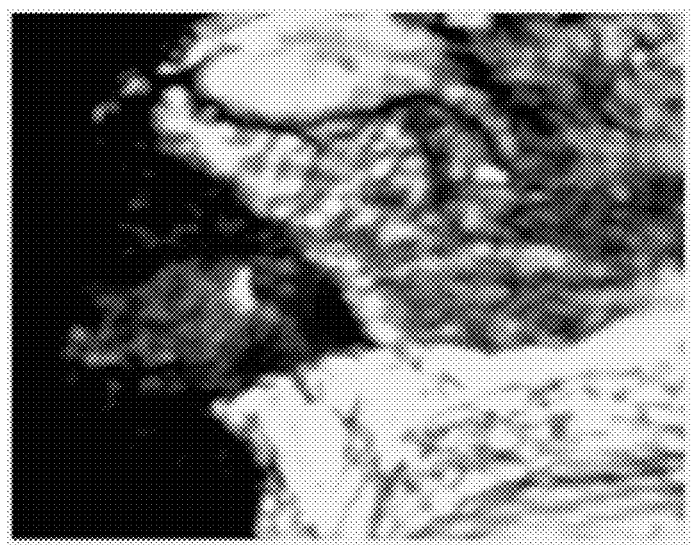
Figure 22E:
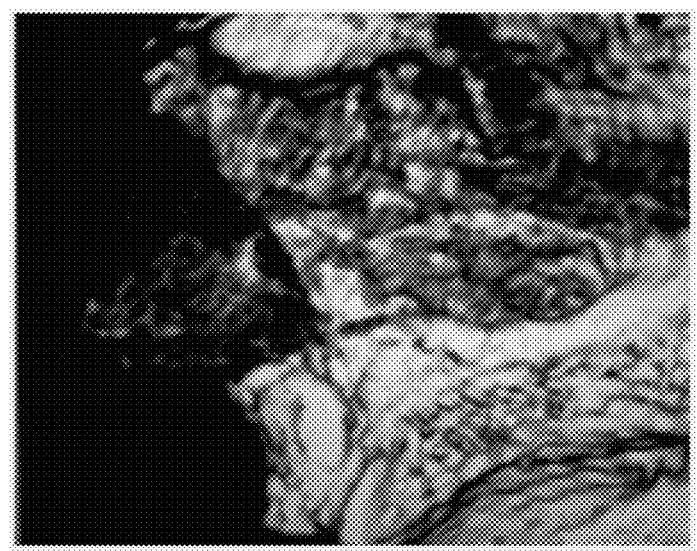

A 22 year old female patient presented with a two year-old rhinoseptoplasty, and a septal fistula (FIG. 22A). She agreed to treatment with formulation 2 of the present invention. Treatment was performed after antisepsis with ESTERICIDE® antiseptic by instilling formulation 2 in both nostrils. Two drops in each nostril, each 12 hours daily until the resolution of the defect. Seven days post-treatment, tomography showed chondrogenesis and partial regeneration of the defect (FIG. 22B). Fifteen days after treatment, reduction of 50% of the size of the fistula was observed (FIG. 22C), concomitant with cartilage's bridges formation and recovery of septum's anatomy (FIGS. 22D-22E).

EXAMPLE 32

Figure 23A:
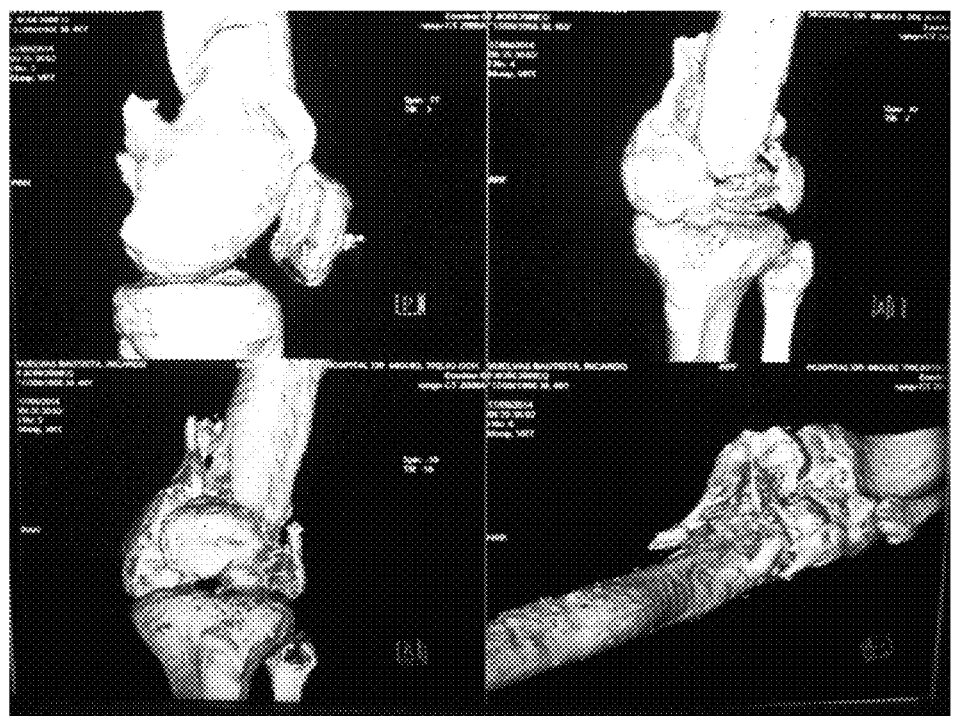
FIGS. 23A-23C are before and after treatment tomographies of a patient with a traumatic right knee arthropathy.
Figure 23B:
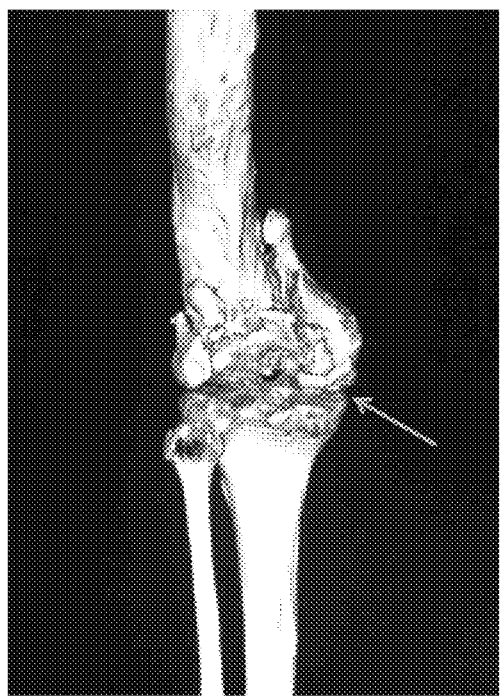
Figure 23C:

Treatment of Left Knee Traumatic Arthropathy with Regeneration of Cartilage and Ligaments A 43 year old male presented with a traumatic right knee arthropathy (FIG. 23A). After antisepsis of the knee surface, lidocaine (2%) was administered via intramuscular infiltration of the knee in a semiflexed position)(45°). Then, 2 mL of formulation 2 was injected in the medial border of the patellar tendon perpendicular to the skin, immediately medial to the patella reaching the articular and synovial capsule. Formulation 2 of the present invention was slowly perfused and a protective dressing of ESTERICIDE® gel was applied over the puncture site. After 21 days, the patient showed remarkable improvement in walking and knee flexibility, as well as chondrogenesis (FIG. 23B). A second application of the formulation was administered a week later as described. After 3 months, the patient's mobility and flexibility was significantly improved. Tomography showed cartilage, bone and ligaments regeneration (FIG. 23C).

EXAMPLE 33

Treatment of Post-traumatic Knee Enthesitis

A 65 year old male presented with a month old traumatic medial ligament enthesitis of the left knee. He experienced pain when walking, sitting down and, when twisting or bending the knee. Reconstructive surgery was indicated, but the patient agreed to be treated with formulation 2 of the present invention. After antisepsis of the knee surface, 2 mL of formulation 2 was injected directly into the medial insertion of the tibial ligament. A protective dressing of ESTERICIDE® gel was applied over the puncture site. Two hours post-treatment the patient reported complete absence of pain. After 15 days, the patient recovered full mobility of the knee and, three months post-treatment the patient remains asymptomatic.

The present invention is well adapted to attain the ends and advantages mentioned as well as inherent therein. The particular disclosed embodiments are illustrative only. The present invention may be modified and practiced in different but equivalent manners apparent to those skilled in the art having benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A formulation consisting of:
   a corticosteroid and
   ascorbic acid, malic acid and citric acid;
   ascorbic acid, lactic acid and citric acid;
   ascorbic acid, malic acid and lactic acid; or
   ascorbic acid, malic acid, lactic acid and citric acid.

2. The formulation of claim 1, wherein said corticosteroid is dexamethasone, cortisol, prednisone, prednisolone, methylprednisolone, betamethasone, triamcinolone, beclometasone, fludrocortisone acetate or deoxycorticosterone acetate.

3. The formulation of claim 2, wherein said dexamethasone is contained in said formulation in an amount from about 0.5 mg/mL to about 10 mg/mL.

4. A method for treating tumors and/or cysts of the jaw, comprising the step:
   contacting said tumors and/or cysts of the jaw with the formulation of claim 1.

5. A method for stimulating growth of a tooth and/or periodontium, comprising the step:
   contacting said tooth and/or periodontium with the formulation of claim 1.

* * * * *